US006210591B1

(12) United States Patent
Krivitski

(10) Patent No.: US 6,210,591 B1
(45) Date of Patent: *Apr. 3, 2001

(54) METHOD TO MEASURE BLOOD FLOW RATE IN HEMODIALYSIS SHUNTS

(75) Inventor: Nikolai M. Krivitski, Ithaca, NY (US)

(73) Assignee: Transonic Systems, Inc., Ithaca, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/348,130

(22) Filed: Jul. 2, 1999

Related U.S. Application Data

(63) Continuation of application No. 09/010,697, filed on Jan. 22, 1998, which is a continuation-in-part of application No. 08/965,975, filed on Nov. 7, 1997, now abandoned, which is a continuation-in-part of application No. 08/305,953, filed on Sep. 16, 1994, now Pat. No. 5,685,989.

(51) Int. Cl.$^7$ .................................................. A61B 5/026
(52) U.S. Cl. ............................ 210/739; 210/85; 210/646; 73/861; 73/861.05
(58) Field of Search .................................... 210/645, 646, 210/739, 745, 746, 805, 85, 93, 96.1, 96.2, 97, 103, 321.6, 929; 73/861.05, 861.06, 861; 604/65, 67; 436/56, 164

(56) References Cited

U.S. PATENT DOCUMENTS

| | | |
|---|---|---|
| 3,640,281 | 2/1972 | Horton . |
| 3,964,479 | 6/1976 | Boag et al. . |

(List continued on next page.)

FOREIGN PATENT DOCUMENTS

| | | |
|---|---|---|
| 0 018 817 | 11/1980 | (EP) . |
| 0 089 003 | 3/1983 | (EP) . |
| 0 373 455 | 6/1990 | (EP) . |
| 255 478 A1 | 4/1988 | (GB) . |
| 521891 | 7/1976 | (RU) . |
| WO 94/27495 | 12/1994 | (WO) . |
| WO 98/17193 | 4/1998 | (WO) . |

OTHER PUBLICATIONS

C. Aldridge et al., The assessment of arteriovenous fistulae created for haemodialysis from pressure and thermal dilution measurements, Journal of Medical Engineering & Technology, May/Jun. 1984, pp. 118–124, vol. 8, No. 3.

Charles B. Anderson, M.D. et al., Blood flow measurements in arteriovenous dialysis fistulas, Surgery, Apr. 1977, pp. 459–461, vol. 81, No. 4.

(List continued on next page.)

*Primary Examiner*—John Kim
(74) *Attorney, Agent, or Firm*—Brian B. Shaw, Esq.; Stephen B. Salai, Esq.; Harter, Secrest & Emery LLP

(57) ABSTRACT

The invention provides a method of determining a shunt flow and particularly for hemodialysis shunts. The method includes determining a shunt flow in a shunt connected between a first point and a second point in a circulating system, wherein a first flow rate is established in the circulating system; a first flow time, or flow velocity is determined between spaced locations in the shunt during the first flow rate in the circulating system; a second flow rate is established in the circulating system; a second flow time, or flow velocity is determined between spaced locations in the shunt during the second flow rate in the circulating system; and a shunt flow is calculated from the first flow time or velocity, the second flow time or velocity, the first flow rate and the second flow rate.

12 Claims, 18 Drawing Sheets

U.S. PATENT DOCUMENTS

| | | |
|---|---|---|
| 3,990,973 | 11/1976 | Boag et al. . |
| 4,081,372 | 3/1978 | Atkin et al. . |
| 4,123,353 | 10/1978 | Hakansson et al. . |
| 4,136,563 | 1/1979 | Mueller et al. . |
| 4,153,554 | 5/1979 | von der Heide et al. . |
| 4,181,610 | 1/1980 | Shintani et al. . |
| 4,231,366 | 11/1980 | Schael . |
| 4,353,368 | 10/1982 | Slovak et al. . |
| 4,391,124 | 7/1983 | Drost et al. . |
| 4,432,231 | 2/1984 | Napp et al. . |
| 4,434,648 | 3/1984 | Drost et al. . |
| 4,508,622 | 4/1985 | Polaschegg et al. . |
| 4,596,550 | 6/1986 | Troutner . |
| 4,650,458 | 3/1987 | Dahlberg et al. . |
| 4,777,958 | 10/1988 | Ophir . |
| 4,797,655 | 1/1989 | Orndal et al. . |
| 4,832,484 | 5/1989 | Aoyagi et al. . |
| 4,856,321 | 8/1989 | Smalling et al. . |
| 4,897,184 | 1/1990 | Shouldice et al. . |
| 4,923,598 | 5/1990 | Schal . |
| 4,938,873 | 7/1990 | Rossi . |
| 4,966,691 | 10/1990 | Brous . |
| 4,995,268 | 2/1991 | Ash et al. . |
| 5,024,756 | 6/1991 | Sternby . |
| 5,100,554 | 3/1992 | Polaschegg . |
| 5,230,341 | 7/1993 | Polaschegg . |
| 5,312,550 | 5/1994 | Hester . |
| 5,385,143 | 1/1995 | Aoyagi . |
| 5,526,808 | 6/1996 | Kaminsky . |
| 5,551,422 | 9/1996 | Simonsen et al. . |
| 5,553,615 | 9/1996 | Carim et al. . |
| 5,642,734 | 7/1997 | Ruben et al. . |
| 5,676,143 | 10/1997 | Simonsen et al. . |
| 5,685,989 | 11/1997 | Krivitski et al. . |
| 5,690,104 | 11/1997 | Kanemoto et al. . |
| 5,720,284 | 2/1998 | Aoyagi et al. . |
| 5,803,908 | 9/1998 | Steuer et al. . |

OTHER PUBLICATIONS

David A. Ogden, M.D. et al., In vivo measurement of blood recirculation during "Y" type single needle dialysis, Journal of Dialysis, 1979, pp. 265–176, vol. 3.

Louk F.I.J. Oudenhoven et al., Magnetic resonance, a new method for measuring blood flow in hemodialysis fistulae, Kidney International, 1994, pp. 884–889, vol. 45.

Emil P. Paganini, MD, FACP, Adapting the dialysis unit to increased hematocrit levels, American Journal of Kidney Diseases, Apr. 1995, pp. S12–S17, vol. 25, No. 4, Suppl. 1.

James L. Porile et al., Preservation of Vascular Access, Journal of the American Society of Nephrology, 1993, pp. 997–1003, vol. 4, No. 4.

Stanley E. Rittgers, PH.D. et al., Noninvasive blood flow measurement in expanded polytetrafluoroethylene grafts for hemodialysis access, Journal of Vascular Surgery, Apr. 1986, pp. 635–642, vol. 3, No. 4, The C.V. Mosby Company, St. Louis, Mo.

Barry S. Strauch, MD, Forecasting thrombosis of vascular access with doppler color flow imaging, American Journal of Kidney Diseases, Jun. 1992, pp. 554–557, vol. XIX, No. 6.

M. Thomas et al., Measurement of vascular access recirculation without contralateral venous puncture, Nephron, 1992, pp. 224–225, vol. 62.

Zbylut J. Twardowski, MD, All currently used measurements of recirculation in blood access by chemical methods are flawed due to intradialytic disequilibrium or recirculation at low flow, American Journal of Kidney Diseases, Dec. 1998, pp. 1046–1058, vol. 32, No. 6.

Zbylut J. Twardowski, Blood recirculation in intravenous catheters for hemodialysis, Journal of the American Society of Nephrology, 1993, pp. 1978–1981, vol. 3, No. 12.

Jeffrey Sands et al., Access flow measured during hemodialysis, ASAIO Journal, Jan.–Feb. 1996, pp. 841–844, vol. 42, No. 1, Lippencott–Raven Publishers.

ASAIO Journal, Jan.–Feb. 1996, p. 74, vol. 42, No. 1, Lippincott–Raven Publishers.

Journal of the American Society of Nephrology, Sep. 1995, p. 501–502, vol. 6, No. 3.

Journal of the American Society of Nephrology, Sep. 1996, p. 1419, vol. 7, No. 9, Williams & Wilki.

Daniel Schneditz et al., Measurement of access flow during hemodialysis using the constant infusion approach, ASAIO Journal, 1998, pp. 74–81.

Richard A. Sherman, MD et al., Assessment of a two needle technique for the measurement of recirculation during hemodialysis, American Journal of Kidney Diseases, Jul. 1991, pp. 80–83, Vo.I. XVIII, No. 1.

Richard A. Sherman, MD et al., Rate–related recirculation: The effect of altering blood flow on dialyzer recirculation, American Journal of Kidney Diseases, Feb. 1991, pp. 170–173, vol. XVII, No. 2.

Richard A. Sherman, MD et al., Recirculation reassessed: The impact of blood flow rate and the low–flow method reevaluated, American Journal of Kidney Diseases, Jun. 1994, pp. 846–848, vol. 23, No. 6.

Richard A. Sherman, MD, The measurement of dialysis access recirculation, American Journal of Kidney Diseases, Oct. 1993, pp. 616–621, vol. 22, No. 4.

Mark C. Shu et al., Flow phenomena in compliant and noncompliant arteriovenous grafts, ASAIO Transactions, Jul.–Sep. 1988, pp. 519–523, vol. 34, No. 3.

Robert R. Steuer et al., Enhanced fluid removal guided by blood volume monitoring during chronic hemodialysis, Artificial Organs, 1998, pp. 627–632, vol. 22, No. 8.

Robert R. Steuer et al., Poster Session—Renal 2: Hematocrit as an indicator of blood volume and a predictor of intradialytic morbid events, ASAIO Journal, Jul.–Sep. 1994, pp. M691–M696, vol. 40.

Robert R. Steuer et al., Reducing symptoms during hemodialysis by continuously monitoring the hematocrit, American Journal of Kidney Diseases, Apr. 1996, pp. 525–532, vol. 27, No. 4.

John C. Van Stone, MD et al., Detection of hemodialysis access outlet stenosis by measuring Outlet resistance, American Journal of Kidney Diseases, Apr. 1994, pp. 562–568, vol. 23, No. 4.

David W. Windus, MD, Permanent vascular access: A nephrologist's view, American Journal of Kidney Diseases, May 1993, pp. 457–471, vol. 21, No. 5.

Von G. Wittenberg et al., Interobserver—Variabilitat von dialyseshuntflubmessungen mit der farbkodierten duplexsonographie, Fortschr Rontgenstr, 1993, pp. 375–378.

J.A. Barra et al., Interet de la debimetrie ultrasonique dans la surveillance post–operatoire et l'evolution des fistules arterio–veineuses pour l'hemodialyse chronique, Journal d'Urologie et de Nephrologie, 1997, pp. 519–525.

Anatole Besarab et al., Determinants of measured dialysis venous pressure and its relationship to true intra–access venous pressure, ASAIO Transactions, Jul.–Sep. 1991, pp. M270–M271, vol. 37, No. 3.

Anatole Besarab et al., The relationship of recirculation to access blood flow, American Journal of Kidney Diseases, Feb. 1997, pp. 223–229, vol. 29, No. 2.

Journal of the American Society of Nephrology, Sep. 1995, p. 1484, vol. 6, No. 3.

Peter J. Bosman et al., Access flow measurements in hemodialysis patients: In vivo validation of an ultrasound dilution technique, Journal of the American Society of Nephrology, Jun. 1996, pp. 966–969, vol. 7, No. 6.

John D. Bower et al., Circulatory function during chronic hemodialysis, ASAIO, pp. 373–377.

B. Charra et al., A dye–dilution cardiac output technique for hemodialyzed patients with arteriovenous fistula, Kidney International, 1973, pp. 51–53, vol. 3.

A.K. Cheung, Stages of future technological developments in haemodialysis, Nephrol Dial Transplant, 1996, pp. 52–58, vol. 11, Suppl. 8.

Valerie De Precigout et al., Comparaison de differentes techniques de surveillance des abords vasculaires chez l'hemodialyse chronique, Nephrologie, 1994, pp. 87–90, vol. 15, No. 2.

Journal of the American Society of Nephrology, Sep. 1995, p. 486, vol. 6, No. 3.

Thomas A. Depner, Nephrology forum—Assessing adequacy of hemodialysis: Urea modeling, Kidney International, 1994, pp. 1522–1535, vol. 45.

ASAIO Journal, Jan.–Feb. 1996, p. 81, vol. 42, No. 1.

Journal of the American Society of Nephrology, Sep. 1996, p. 1407, vol. 7, No. 9.

R.D. Gleed et al., Validation in the sheep of an ultrasound velocity dilution technique for haemodialysis graft flow, Nephrology Dialysis Transplantation, 1997, pp. 1464–1467, vol. 12.

Robert L. Hester, Ph.D. et al., A new technique for determining recirculation in the ESRD Patient, Nephrology News & Issues, Jun. 1993, pp. 44–45.

Robert L. Hester, Ph.D. et al., The determination of hemodialysis blood recirculation using blood urea nitrogen measurements, American Journal of Kidney Diseases, Dec. 1992, pp. 598–602, vol. XX, No. 6.

N.A. Hoenich et al., A technique for the laboratory determination of recirculation in single needle dialysis, The International Journal of Artificial Organs, pp. 63–70, vol. 16, No. 2.

Nicholas Andrew Hoenich et al., Technology and clinical application of large–bore and implantable catheters, Artificial Organs, pp. 276–282, vol. 18, No. 4.

Jacobo Kelber, MD et al., Factors affecting kidney delivery of high–efficiency dialysis using temporary vascular access, American Journal of Kidney Diseases, Jul. 1993, pp. 24–29, vol. 22, No. 1.

Barry Kirschbaum, MD et al., Study of vascular access blood flow by angiodynography, American Journal of Kidney Diseases, Jan. 1995, pp. 22–25, vol. 25, No. 1.

H.W. Klempt et al., Ergebnisse der farbstoffverdunnungstechnik bei peripheren, arteriovenosen fisteln und hyperthyreosen, Eingegangen, Jan. 1975, pp. 863–878, vol. 64.

Nikolai M. Krivitski, Ph.D. et al., Accuracy of dilution techniques for access flow measurement during hemodialysis, American Journal of Kidney Diseases, Mar. 1998, pp. 502–508, vol. 31, No. 3.

Nephrology Dialysis Transplantation, Sep. 1997, p. A129, vol. 12, No. 9.

Journal of the American Society of Nephrology, Sep. 1997, p. 164A, vol. 8.

Journal of the American Society of Nephrology, Sep. 1997, p. 155A, vol. 8.

Journal of the American Society of Nephrology, Sep. 1995, p. 1496, vol. 6, No. 3.

Nikolai M. Krivitski, Novel method to measure access flow during hemodialysis by ultrasound velocity dilution technique, ASAIO Journal, Jul.–Sep. 1995, pp. M741–M744, vol. 41, No. 3.

Journal of the American Society of Nephrology, Sep. 1996, p. 1410, vol. 7, No. 9.

Nikolai M. Krivitski, Theory and validation of access flow measurement by dilution technique during hemodialysis, Kidney International, 1995, pp.244–250, vol. 48.

ASIAO Journal, Jan.–Feb. 1996, p. 80, vol. 42, No. 1, Lippincott–Raven Publishers.

D. Krpan et al., Measurement of blood flow through AV–fistulae by means of Doppler sonography in regularly haemodialysed patients, 1992, pp.78–82, vol. 14, No. 2.

Kazuyoshi Kubota et al., Arteriovenous shunt flow measurement by ultrasonic duplex system, ASAIO Transactions, Jul.–Sep. 1987, pp.144–146, vol. 33, No. 3.

B.M.T. Lantz et al., Determination of blood flow through arteriovenous fistulae and shunts, Acia Radiological Diagnosis, 1979, pp. 727–736, vol. 20.

Robert M. Lindsay et al., A comparison of methods for the measurement of hemodialysis access recirculation, ASAIO Journal, 1988, pp. 191–193.

Journal of the American Society of Nephrology, Sep. 1996, p. 1412, vol. 7, No. 9.

Robert M. Lindsay et al., A device and a method for rapid and accurate measurement of access recirculation during hemodialysis, Kidney International, 1996, pp. 1152–1160, vol. 49.

Robert M. Lindsay, Assessment of access recirculation during haemodialysis, Current Opinion in Nephrology and Hypertension, 1997, pp. 570–574, vol. 6.

Robert M. Lindsay, Hemodialysis access blood flow rates can be measured by a differential conductivity technique and are predictive of access clothing, American Journal of Kidney Diseases, Oct. 1997, pp. 475–482, vol. 30, No. 4.

F. Lopot, Use of continuous blood volume monitoring to detect inadequately high dry weight, The International Journal of Artificial Organs, 1996, pp. 411–414.

Richard E. May, Predictive measures of vascular access thrombosis: A prospective study, Kidney International, 1997, pp. 1656–1662, vol. 52.

D.A. Ogden, Blood recirculation during hemodialysis with a coaxial counterflow single needle blood access catheter, ASAIO Transactions, Apr. 20–21, 1979, pp. 325–327, vol. 25.

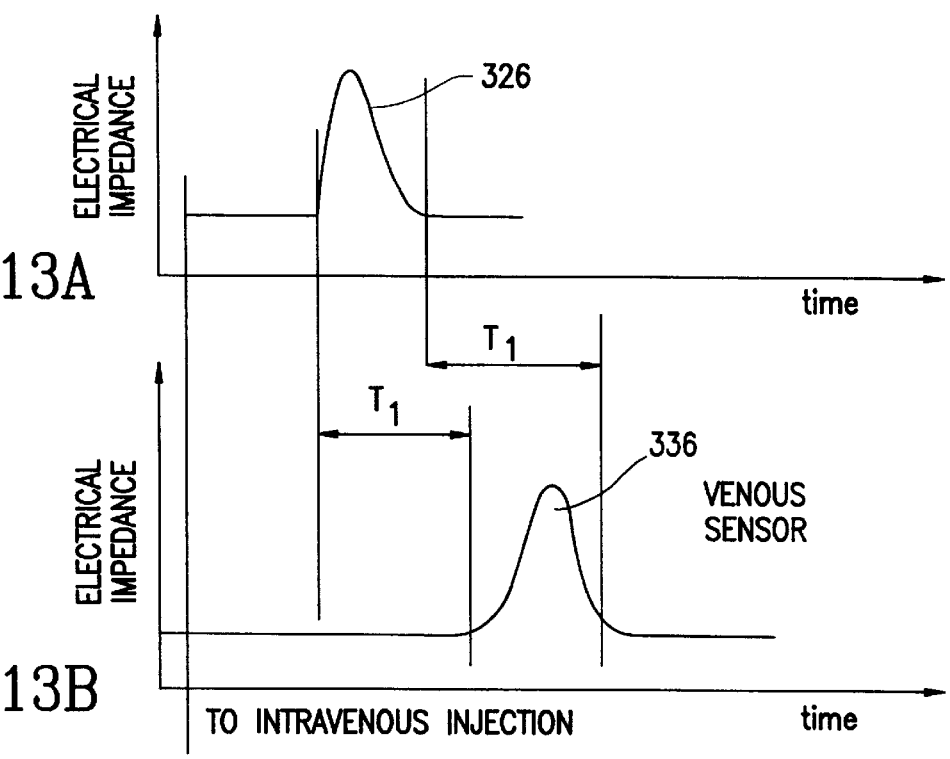
FIG. 13A
FIG. 13B
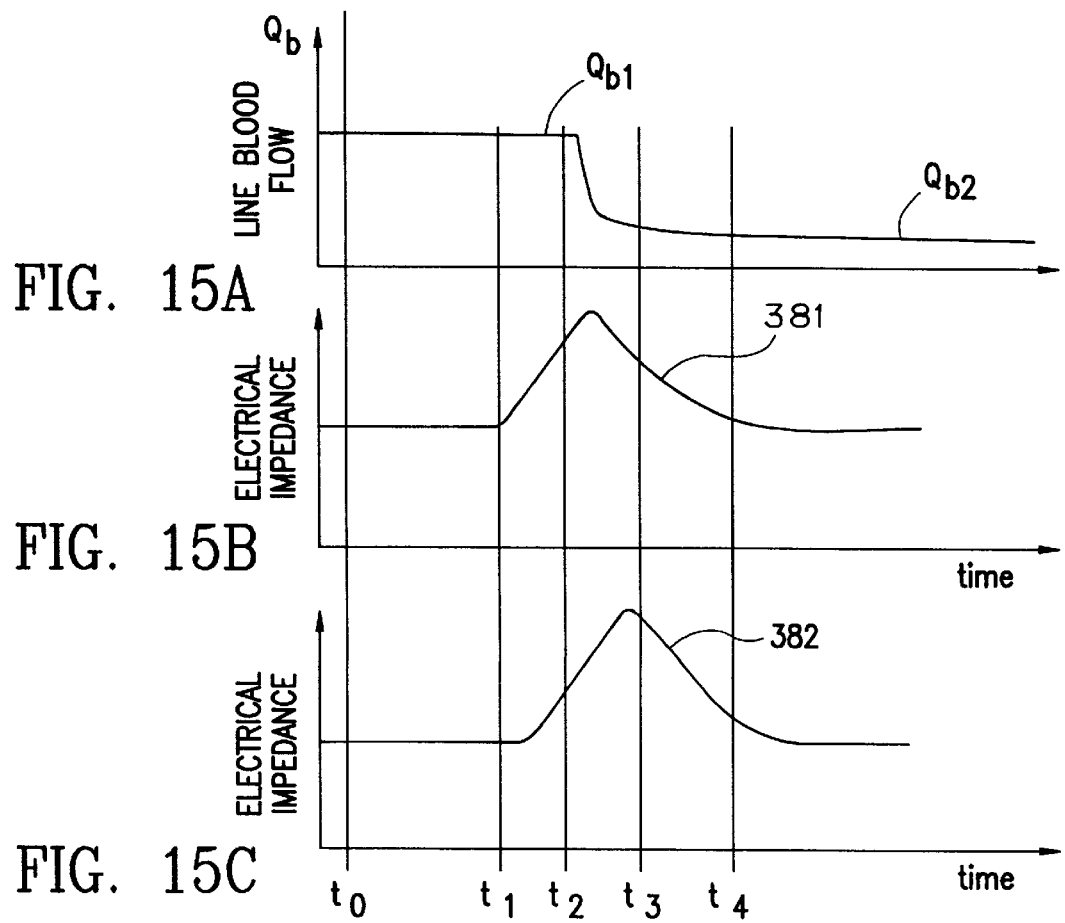
FIG. 15A
FIG. 15B
FIG. 15C

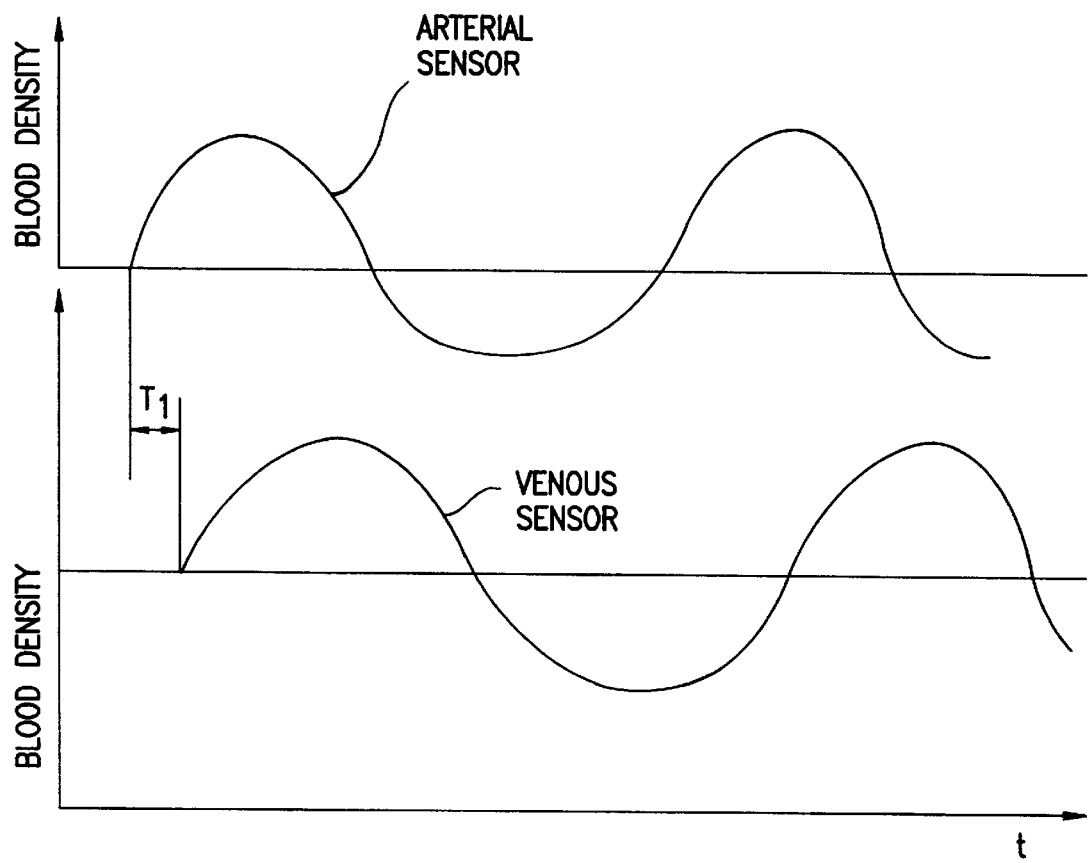

METHOD TO MEASURE BLOOD FLOW RATE IN HEMODIALYSIS SHUNTS

REFERENCE TO RELATED APPLICATIONS

This is a continuation of application Ser. No. 09/010,697, filed Jan. 22, 1998 now pending, which is a continuation-in-part of copending application Ser. No. 08/965,975, filed Nov. 7, 1997, abandoned, which is a continuation-in-part of application Ser. No. 08/305,953 filed Sep. 16, 1994, which issued as U.S. Pat. No. 5,685,989 on Nov. 11, 1997.

FIELD OF THE INVENTION

The invention pertains to the field of blood treatment or measurement systems, and in particular, to processes for measuring arteriovenous shunt blood flow during hemodialysis.

BACKGROUND OF THE INVENTION

Hemodialysis is a process by which an artificial kidney replaces the function of a patient's kidney. Blood is removed from the patient's vascular system via suitable equipment such as an arterial needle, tube, or line, is passed through a dialyzer and is returned to the patient via a venous needle, tube, or line for normal circulation through the patient's vascular system. A majority of dialysis patients have an arteriovenous shunt implanted to create a location having a high blood flow that simplifies the withdrawal of blood through a line connected to the part of the shunt that is closer to the arterial side of the shunt and the return of purified blood through a line connected to the shunt downstream of the withdrawal site, closer to venous side of the shunt. In some cases the shunt clots or stenoses with the resulting reduction in blood flow necessitates surgery that is costly and invasive for the patient. If there is low blood flow in the shunt or any other problem with the venous outflow, some part of the freshly dialyzed blood from the venous return line flows directly to the arterial withdrawal line where it is again filtered. This access recirculation is a well-known problem during hemodialysis, and if such undesired direct recirculation is at a high enough level, some amount of blood is repeatedly refiltered so that the rest of the patient's blood is not sufficiently filtered for adequate dialysis.

One method of measuring shunt blood flow currently uses color coded duplex sonography. This is very expensive and involves operation by highly qualified professionals. Measurements are therefore made only rarely, so that the onset of reduced flow is not detected at a time when the problem can be corrected without surgery.

The standard test for undesired direct recirculation requires three blood samples while the patient is on dialysis. This method requires blood samples from the patient, time from the nurses, and high laboratory costs. Since dialysis patients generally have lower hematocrit than the normal population and are at greater risk from losing blood, this test is not very satisfactory.

Another technique for measuring access recirculation involves introducing an indicator, such as a saline solution, into the venous line and recording changes of blood properties due to the presence of the indicator in the arterial line. The problem with this technique is that the indicator can reenter the arterial line by two pathways: directly by the access shunt ("shunt recirculation") and by way of the patient's cardiopulmonary pathway. Existing technologies cannot separate shunt recirculation from cardiopulmonary recirculation (CPR). This can led to a false diagnosis of shunt recirculation in cases where only CPR is present.

SUMMARY OF THE INVENTION

The present invention avoids the problem encountered with previous methods and techniques by providing an accurate determination of shunt blood flow and recirculation at lower cost. In particular, it provides methods and techniques for identifying access recirculation with high specificity so as to permit accurate measurement of undesirable shunt in the presence of normal (and desirable) cardiopulmonary recirculation.

Briefly stated, a device for determining shunt flow in a hemodialysis shunt connected between two points in a cardiovascular-hemodialysis system includes a flow sensor connected to either the hemodialysis inflow (arterial) line or the outflow (venous) line. An indicator is preferably introduced into the system that is sensed by first and second sensors that are spaced apart and disposed effective for sensing the indicator at two locations in the cardiovascular-hemodialysis system. Natural indicators produced by the body, such as density variations in the blood caused by rhythmic breathing, are optionally used instead of an introduced indicator. A detector connected to the flow sensor and the first and second sensors determines, at a first flow rate, a first time a first indicator takes to move between the two locations, and at a second flow rate, a second time a second indicator takes to move between the two locations. The shunt flow is then calculated from the first and second times and the first and second flow rates.

According to an embodiment of the invention, a method for determining shunt flow in a shunt connected between first and second points in a circulating system includes the steps of:
  a) establishing a first flow rate in the circulating system,
  b) measuring, during the first flow rate, a first time a first indicator takes to move between a first location and a second location, the first and second locations being within the shunt,
  c) establishing a second flow rate in the circulating system,
  d) measuring, during the second flow rate, a second time a second indicator takes to move between the first location and the second location, and
  e) calculating the shunt flow from the first and second times and the first and second flow rates.

According to an embodiment of the invention, a method for determining shunt flow in a shunt connected between first and second points in a circulating system includes the steps of:
  a) establishing a first flow rate in the circulating system;
  b) determining, during said first flow rate, a first time it takes for an indicator to move from a first location to a second location;
  c) establishing a second flow rate in the circulating system;
  d) determining, during the second flow rate, a second time it takes for the indicator to move from the first location to the second location; and
  e) calculating the shunt flow from the first and second times and the first and second flow rates.

According to an embodiment of the invention, a method for determining shunt flow in a shunt connected between first and second points in a circulating system includes the steps of:
  a) establishing a first flow rate in the circulating system,
  b) measuring, during the first flow rate, a first time a first indicator takes to move between a first location and a second location, the first location being within the circulating system at a known position, and the second location being in the shunt, c) establishing a second flow rate in the circulating system, d) measuring, during the second flow rate, a second time a second indicator takes to move between the first location and the second location, and e) calculating the shunt flow from the first and second times and the first and second flow rates.

According to an embodiment of the invention, a device for determining shunt flow in a shunt connected between first and second points in a circulating system includes first means for establishing a first flow rate in the circulating system; first means for measuring, during the first flow rate, a first time a first indicator takes to move between a first location and a second location, the first and second locations being within the shunt; second means for establishing a second flow rate in the circulating system; second means for measuring, during the second flow rate, a second time a second indicator takes to move between the first location and the second location; and means for calculating the shunt flow from the first and second times and the first and second flow rates.

According to an embodiment of the invention, a device for determining shunt flow in a shunt connected between first and second points in a circulating system includes first means for establishing a first flow rate in the circulating system; first means for determining, during the first flow rate, a first time it takes for an indicator to move from a first location to a second location; second means for establishing a second flow rate in the circulating system; second means for determining, during the second flow rate, a second time it takes for the indicator to move from the first location to the second location; and means for calculating the shunt flow from the first and second times and the first and second flow rates.

According to an embodiment of the invention, a device for determining shunt flow in a shunt connected between first and second points in a circulating system includes first means for establishing a first flow rate in the circulating system; first means for measuring, during the first flow rate, a first time a first indicator takes to move between a first location and a second location, the first location being within the circulating system at a known position, and the second location being in the shunt; second means for establishing a second flow rate in the circulating system; second means for measuring, during the second flow rate, a second time a second indicator takes to move between the first location and the second location; and means for calculating the shunt flow from the first and second times and the first and second flow rates.

According to an embodiment of the invention, a device for determining shunt flow in a shunt connected between first and second points in a circulating system includes a flow sensor connected to the circulating system; first and second sensors spaced apart and disposed effective for sensing an indicator at first and second locations in the circulating system; a detector connected to the flow sensor and the first and second sensors, wherein at a first flow rate, a first time a first indicator takes to move between the first location and the second location is determined; and at a second flow rate, a second time a second indicator takes to move between the first and second locations is determined; and means for calculating the shunt flow from the first and second times and the first and second flow rates.

According to an embodiment of the invention, a method for determining shunt flow in a shunt connected between first and second points in a circulating system includes the steps of:

a) establishing a distance between a first location in the shunt and a second location in the shunt, b) measuring an average time an indicator takes to move between the first location and the second location, c) providing an average cross-section area of the shunt, and d) calculating the shunt flow from the average time, the distance, and the average cross-section area.

According to an embodiment of the invention, a device for determining shunt flow in a shunt connected between first and second points in a circulating system includes means for establishing a distance between a first location in the shunt and a second location in the shunt; means for measuring an average time an indicator takes to move between the first location and the second location; and means for calculating the shunt flow from the average time, the distance, and a known average cross-section area of the shunt.

According to an embodiment of the invention, a method for determining shunt blood flow in a shunt connected between first and second points in a circulating system includes the steps of:

establishing a blood flow rate in the system;

establishing a distance between first and second locations in the shunt;

determining an average time it takes for blood to travel between the first and second locations at the blood flow rate;

providing an average cross-section area of the shunt; and calculating the shunt blood flow from the blood flow rate, the distance, the time, and the average cross-section area.

According to an embodiment of the invention, a device for determining shunt blood flow in a shunt connected between first and second points in a circulating system includes means for establishing a distance between a first location in said shunt and a second location in the shunt; means for establishing a blood flow rate in the system; means for measuring an average time blood takes to move between the first location and the second location at the blood flow rate; and means for calculating the shunt blood flow from the blood flow rate, the average time, the distance, and a known average cross-section area of the shunt.

BRIEF DESCRIPTION OF THE DRAWINGS

FIG. 13A shows the arterial sensor dilution curve for an introduced indicator.

FIG. 13B shows the venous sensor dilution curve for the introduced indicator producing the curve of FIG. 13A.

FIG. 14A shows the arterial sensor curve for changing blood densities due to breathing.

FIG. 14B shows the venous sensor curve for changing blood densities due to breathing.

FIG. 15A shows the line blood flow at times t0, t1, t2, t3, and t4.

FIG. 15B shows the arterial sensor dilution curve for an introduced indicator.

FIG. 15C shows the venous sensor dilution curve for the introduced indicator producing the curve of FIG. 15B.

DESCRIPTION OF THE PREFERRED EMBODIMENT

Figure 1A:
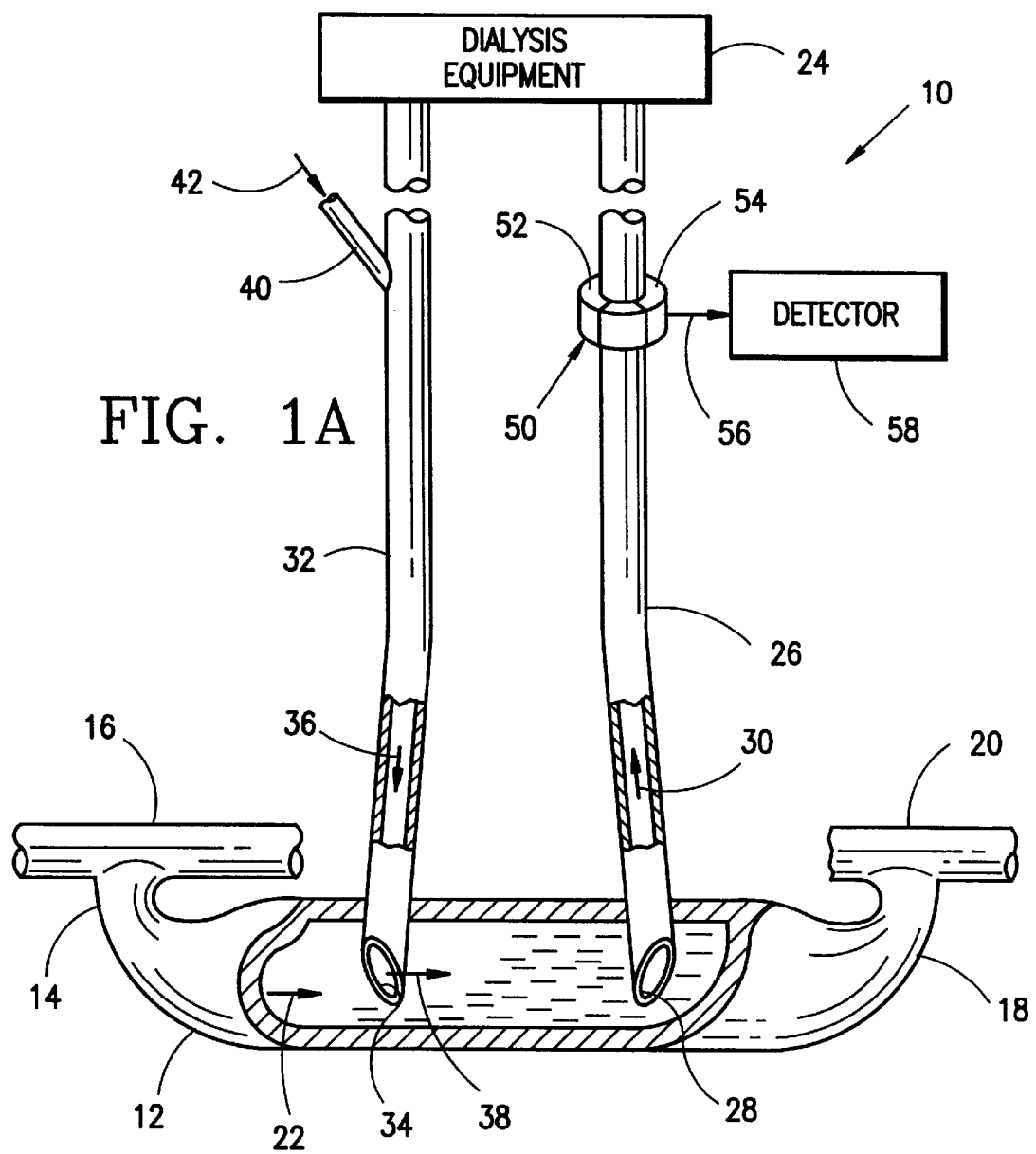
FIG. 1A is a diagrammatic illustration of an arteriovenous shunt connected by way of arterial and venous tubes to a dialyzer with an arterial tube inlet in the shunt downstream from a venous tube outlet, an injection port in the venous tube, and a sensor for the arterial tube.

Blood flow, Q, measured by the dilution method as taught in A. C. Guyton, *Textbook of Medical Physiology*, Sixth Edition, p. 287 (1981) is given by:

$$Q = \frac{V}{S}, \tag{Eq. 1}$$

where V is the amount of injected indicator and S is the area under a dilution curve and is equal to the average concentration of indicator in the blood for the duration of the curve, multiplied by the duration of the curve.

A dilution curve is obtained by measuring changes in a physical parameter of the blood over a period of time, and plotting the resulting variations. For example, if the blood parameter being measured is sound velocity, the injection of an indicator such as a saline solution, having a different sound velocity than blood, will produce a change in the measured parameter as the indicator passes the sensor location. The indicator dilutes the blood, and produces a sound velocity curve which is a measure of that dilution. Although injection of a saline solution is convenient for producing a measurable change in a blood parameter such as sound velocity, other changes of parameters may also be suitable.

Thus, changes in any physical or chemical parameters of blood such as temperature, electrical impedance, blood urea concentration, optical characteristics, and the like may be obtained by the introduction or withdrawal of suitable indicators to produce blood parameter changes. Furthermore, those skilled in the art may induce changes in blood parameters of longer duration, and record only a part of the resulting indicator dilution curve, such as its quasi-steady state level change. For purposes of this disclosure, reference will primarily be made to the use of saline solution as the indicator, with resulting changes in sound velocity in the blood being measured to provide a dilution curve, but it will be understood that other indicators and other measurement strategies may be used to vary corresponding parameters for obtaining dilution measurements.

To facilitate the measurement of shunt blood flow in accordance with the present invention, the blood line connection is reversed from normal; that is, the arterial inlet which removes the blood from the patient for dialysis is located downstream (not upstream as normal) of the venous outlet in the shunt. A volume of indicator, such as a saline solution, is injected into the venous line ($V_{ven}$), where it is mixed with the dialyzer blood flow $Q_{dial}$ and the mixture is delivered to the shunt where it is combined with the blood flow in the shunt ($Q_{sh}$). The blood shunt flow ($Q_{sh}$) can be calculated from Equation 1 by measuring the dilution area in the arterial line $S_{art}$:

$$Q_{sh} + Q_{dial} = \frac{V_{ven}}{S_{art}} \tag{Eq. 2}$$

$$Q_{sh} = \frac{V_{ven}}{S_{art}} - Q_{dial} \tag{Eq. 3}$$

Equation 3 shows that if the blood flow through the dialyzer $Q_{dial}$ is measured and the absolute concentration of indicator in the arterial blood line $S_{art}$ is recorded, then the blood flow through the shunt $Q_{sh}$ can be calculated.

In some methods applicable to hemodialysis, sensors are clamped onto the exterior of the arterial or venous line, or tube. However, it is difficult to measure the absolute concentration of indicator in the blood through the hemodialysis tube. For example, if a sound velocity sensor is used to record protein concentration changes in blood due to a saline indicator injection, the sound beam will have to pass through both the tube and the blood. Recorded measurements of absolute sound velocity will be influenced not only by the blood, but also by the unknown sound properties of the tube. The same problem occurs if an optical sensor is clamped onto tube; i.e., the recorded amplitude of a light beam is not only the function of hemoglobin concentration but of tube properties.

This problem may be solved by an additional calibration injection of the same indicator, which is injected in the arterial line, but upstream of the place where the measurements are made. The equation for this case will be:

$$Q_{dial} = \frac{V_{cal}}{S_{cal}}, \qquad (Eq. 4)$$

where $V_{cal}$ is the known quantity of indicator in the calibration injection and $S_{cal}$ is the area under the resulting dilution curve. This area is the average concentration of indicator in the blood for the duration of the curve, times the duration of the curve.

From Equations 2 and 4, the formula for shunt blood flow are:

$$Q_{shunt} = Q_{dial}\left(\frac{V_{ven} \times S_{cal}}{V_{cal} \times S_{art}} - 1\right) \qquad (Eq. 5)$$

$$Q_{shunt} = \left(\frac{V_{ven}}{S_{art}} - \frac{V_{cal}}{S_{cal}}\right). \qquad (Eq. 6)$$

Equation 5 is suitable if blood flow in the tube can be measured accurately. The ratio $S_{cal}/S_{art}$ shows that the recorded dilution areas only need to be proportional to relative changes in concentrations in this case. Assuming that tube properties are constant during the measurements, the value of this ratio can be calculated with high accuracy for most types of sensors, including sound velocity, optical, etc.

Equation 6 can be used where tube blood flow is unknown but absolute concentrations are measured, such as, for instance, by withdrawing the blood from the arterial blood line and using an optical densitometer for optical dye dilution measurements.

To avoid the need for a calibration injection, an additional sensor that is matched to the arterial line sensor is located on the venous line downstream of the location of the intravenous indicator injection. For this case, the injected indicator will be mixed with the venous line tube flow, so by analogy with the calibration injection of Equation 4:

$$Q_{dial} = V_{ven}/S_{ven} \qquad (Eq. 7)$$

where $S_{ven}$ is the area under the dilution curve and is calculated as the average concentration of indicator in the blood for the duration of the curve, times the duration of the curve. From the same injection, the area $S_{art}$ is generated. The formula for blood flow by substituting in Equation 5 is:

$$Q_{shunt} = Q_{dial}\left(\frac{S_{ven}}{S_{art}} - 1\right). \qquad (Eq. 8)$$

As an alternative to the foregoing, a measurement of the quantity of blood recirculation may be made during a normal connection of the dialysis blood lines of the shunt, with the intake to the arterial line being upstream in the shunt and the outlet of the venous line connection being downstream in the shunt. With this "normal" connection, after injecting an indicator into the venous line, a rapid appearance of indicator in the arterial line is an indication that recirculation exists. The quantity of recirculation is the fraction of freshly filtered blood in the venous line that recirculates to the arterial line and this quantity is equal to the ratio of indicator volume that is recirculated into the arterial line ($V_{rec}$) to the volume that was injected into the venous line ($V_{ven}$).

The amount of recirculated indicator $V_{rec}$ is equal to the area under the recirculated concentration dilution curve $S_{rec}$ multiplied by the dialysis blood flow in the arterial line $Q_{dial}$:

$$V_{rec} = S_{rec} \times Q_{dial} \qquad (Eq. 9)$$

The same problem with the evaluation of $S_{rec}$ that was described for Equations 2 and 3 persists; namely, the difficulty of measuring indicator concentration through the tubing. This problem is avoided by an additional calibration injection of the same indicator into the arterial line upstream from the place where the measurements are made, as discussed above with respect to Equation 4. From Equations 4 and 9, the circulating fraction is:

$$\frac{V_{rec}}{V_{ven}} = \frac{V_{cal}}{V_{ven}} \times \frac{S_{rec}}{S_{cal}}. \qquad (Eq. 10)$$

The ratio $S_{rec}/S_{cal}$ in Equation 10 indicates that the measured dilution areas need only be in the same relative units. Assuming that tube properties are constant during the measurements, this ratio can be calculated with high accuracy for most types of sensors; e.g., sound velocity, optical, etc.

To avoid the need for a calibration injection, an additional sensor that is matched to the arterial line sensor may be located on the venous line downstream of the location of the intravenous indicator injection. For this case, the injected indicator will be mixed with the venous line flow, so by analogy with the calibration injection Equation 7:

$$\frac{V_{rec}}{V_{ven}} = \frac{S_{rec}}{S_{ven}}. \qquad (Eq. 11)$$

In summary, the, shunt blood flow can be measured by reversing arterial and venous blood lines. An arterial inlet, which removes blood from a patient's vascular system, is located in the shunt downstream of a venous outlet, which returns treated blood to the patient's vascular system. An indicator material is injected into an injection port in the venous tube, and changes in the physical properties of the blood are monitored in the arterial line. These changes are recorded, with the area under the resulting dilution curve providing a measure of blood flow in the shunt and tube line. The indicator used for this purpose is any material or blood treatment which changes the physical characteristics of the blood. For example, it can be a saline solution, preferably of known concentration, or can be a heating or cooling of a quantity of blood. The change of characteristics is measured by known sensors, such as sound velocity sensors, electrical impedance sensors, optical sensors, thermal sensors, isotope sensors, or the like, and the blood flow relationships are calculated in accordance with the foregoing equations.

Because the tubing used to carry blood from the patient to the dialysis equipment introduces errors into the measurements of blood flow, calibration measurements may be required using a calibration injection, and if blood flow is unknown, blood concentration measurements. To avoid the need for a calibration injection, an additional sensor may be provided on the venous line downstream of the venous injection port.

Blood recirculation can also be measured with the arterial inlet located in the shunt upstream of the venous outlet. In this case, the indicator is injected into an injection port in the venous line outlet (as before) and the blood characteristics are monitored in the arterial line. A calibration injection may be provided at an injection port in the arterial line upstream of the arterial tube monitor, or to avoid a calibration injection, a second blood characteristic monitor can be provided in the venous tube downstream of the venous injection port.

As noted above, recirculation of treated blood occurs not only in the dialysis shunt, but in the patient's regular cardiovascular circuit, with the result that an indicator flowing from the venous line can reach the arterial line by two different pathways. The cardiovascular recirculation always exists, since it is a normal functional parameter of the patient's heart, and is not a result of a malfunction in the dialysis process. As a result, an injected indicator will always appear in the arterial line leading to the dialysis equipment, and it is therefore of primary importance that this CPR be separated from shunt recirculation for correct diagnosis of the adequacy of the dialysis procedure. This separation is carried out, in accordance with the invention, by a further diagnosis of the indicator dilution curve recorded by the arterial line sensor upon introduction of a venous indictor bolus.

One way to achieve the foregoing separator between shunt recirculation and CPR is by analysis of the expected appearance time of shunt recirculation, if it exists, and the observed time at which it actually occurs. Shunt recirculation generally appears before CPR.

Another method for achieving separation between shunt recirculation and CPR is by waveform analysis of recirculation curves obtained from measurements of the indicator. Shunt recirculation curves have a pulsatile shape, while CPR produces a smooth curve which is longer in duration.

Finally, the two types of recirculation can be separated from a combination of the measurement of time of arrival and waveform shape analysis.

Figure 1B:
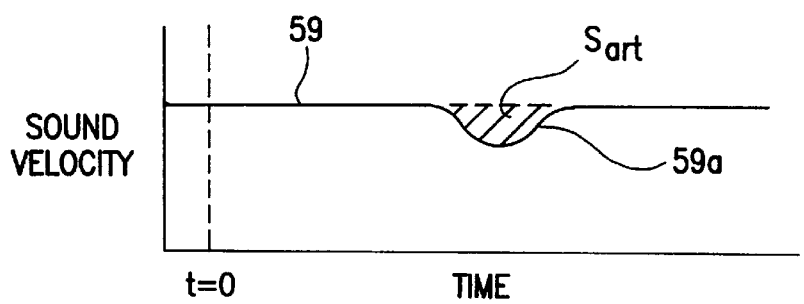
FIG. 1B illustrates a dilution curve for the device of FIG. 1A.

Referring now to FIG. 1, a first embodiment of a patient blood dialysis system 10 is shown which uses a reversed connection of arterial and venous lines to a blood vessel 12 illustrated as an arteriovenous shunt connected at its upstream end 14 to a patient's artery 16 and connected at its downstream end 18 to a patient's blood vein 20. The shunt may be an artificial vessel or a native vessel that is surgically moved between artery 16 and vein 20. The direction of flow of blood in the vessel 12 is indicated by arrow 22 and it is this blood flow which is to be determined. Connected between vessel 12 and conventional blood dialysis equipment 24 is an arterial line, such as a tube 26, having an inlet 28 in the shunt 12 for drawing blood for treatment by the dialysis equipment. The direction of flow of blood in arterial line 26 is illustrated by arrow 30.

Also connected between the dialysis equipment 24 and shunt 12 is a venous line, or tube, 32 which carries treated blood from the dialysis equipment 24 back to the shunt. The venous line 32 has an outlet 34 located in shunt 12, upstream of the arterial line inlet 28. The direction of flow of treated blood in venous line 32 is illustrated by arrow 36. As illustrated by arrow 38, treated blood from the outlet 34 travels downstream, in the direction of the main flow 22, toward the inlet 28 where some of the treated blood 38 is collected by the arterial line 26.

Measurement of blood flow in the shunt is obtained, in accordance with the invention, by injecting into venous line 32, as by way of an injection port 40, an indicator material having a selected physical property differing from that of the blood being treated. In the preferred embodiment, this material, indicated by arrow 42, is a saline solution which is isotonic with the blood but which has different sound velocity properties. Other indicator materials may be, for example, heated or cooled blood. The injected indicator is mixed with the blood flow 36 in the venous line and is returned to shunt 12 where it is mixed with the shunt flow 22. A portion of the indicator is withdrawn from the shunt by the arterial blood line, as indicated by arrow 30.

A sensor 50 is provided at a location downstream of the injection port 40, which is preferably located in the arterial line 26, as illustrated in FIG. 1. The sensor preferably is a blood sound velocity detector which includes a sound source 52 sending a sound beam directly through the blood passing through arterial line 26 to a sound receiver 54 which produces an output signal related to the velocity of sound in the blood. Such sound velocity sensors are well-known in the art and are exemplified by the Transonic 4× perivascular probe manufactured by Transonic Systems, Inc., Ithaca, N.Y., U.S.A. In this probe, the receiver 54 produces an output signal on line 56 which is directed to a detector 58. Detector 58 measures and evaluates the signal supplied by way of line 56. The detector 58 records the signal and carries out the calculations described above for converting the sensor output signal to a blood concentration signal for determination of the blood flow in the shunt 12 and through the dialysis equipment 24. If the blood flow in the dialysis equipment 24 is significant in comparison to the flow in shunt 12, the measurements made by sensor 50 give results which overstate the flow of the shunt.

More particularly, the blood flow Q in shunt 12 may be calculated in accordance with Equation 1 by calculating the area under the dilution curve obtained by sensor 50. An example of such a curve is illustrated in FIG. 1A, wherein the velocity of sound in the arterial blood flow is illustrated by curve 59. At time 0, an indicator material is injected at port 40, and at some later time, the change in sound velocity caused by the indicator is detected at sensor 50 as illustrated by the dip shown as dilution area 59a in curve 59. The area under the dilution curve 59 in region 59a is the area $S_{art}$ described in Equation 2.

Figure 2:
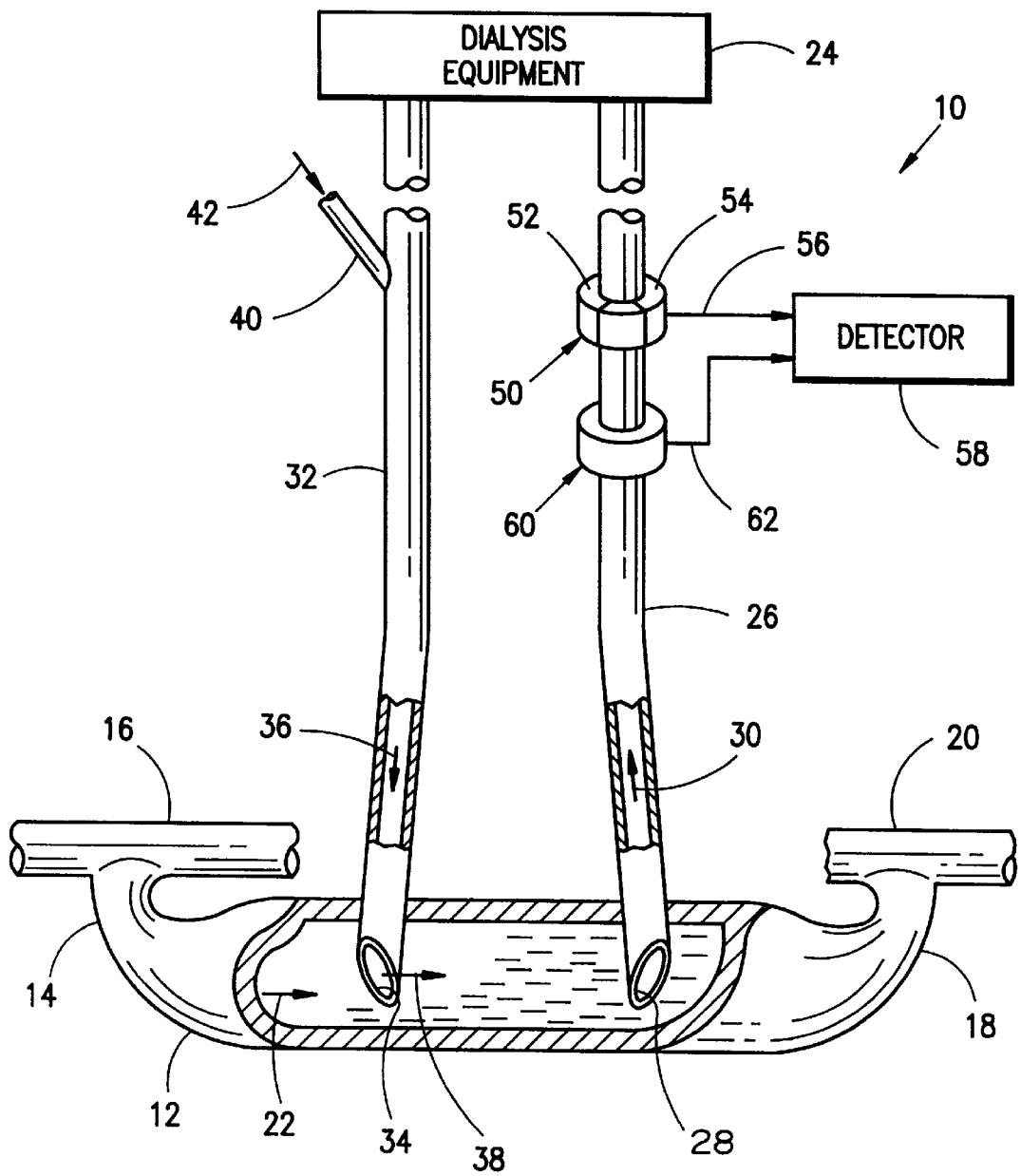
FIG. 2 is a modification of FIG. 1A, adding a second sensor for the arterial tube.

Referring to FIG. 2, a second blood flow sensor 60 may be provided on arterial line 26 and connected by way of line 62 to the detector 58. This second sensor is a blood flow sensor such as a model HT109 clamp-on flowmeter produced by Transonic Systems, Inc., which is used to measure the blood flow $Q_{dial}$ in line 26 so that it can be subtracted from the sum of flows calculated in accordance with the embodiment of FIG. 1 to increase the accuracy of the shunt blood flow determination. This improved accuracy is obtained in accordance with Equations 2 and 3. Although sensor 60 is shown as separate from sensor 50, the two sensors may be incorporated into a single unit if desired.

Figure 3A:
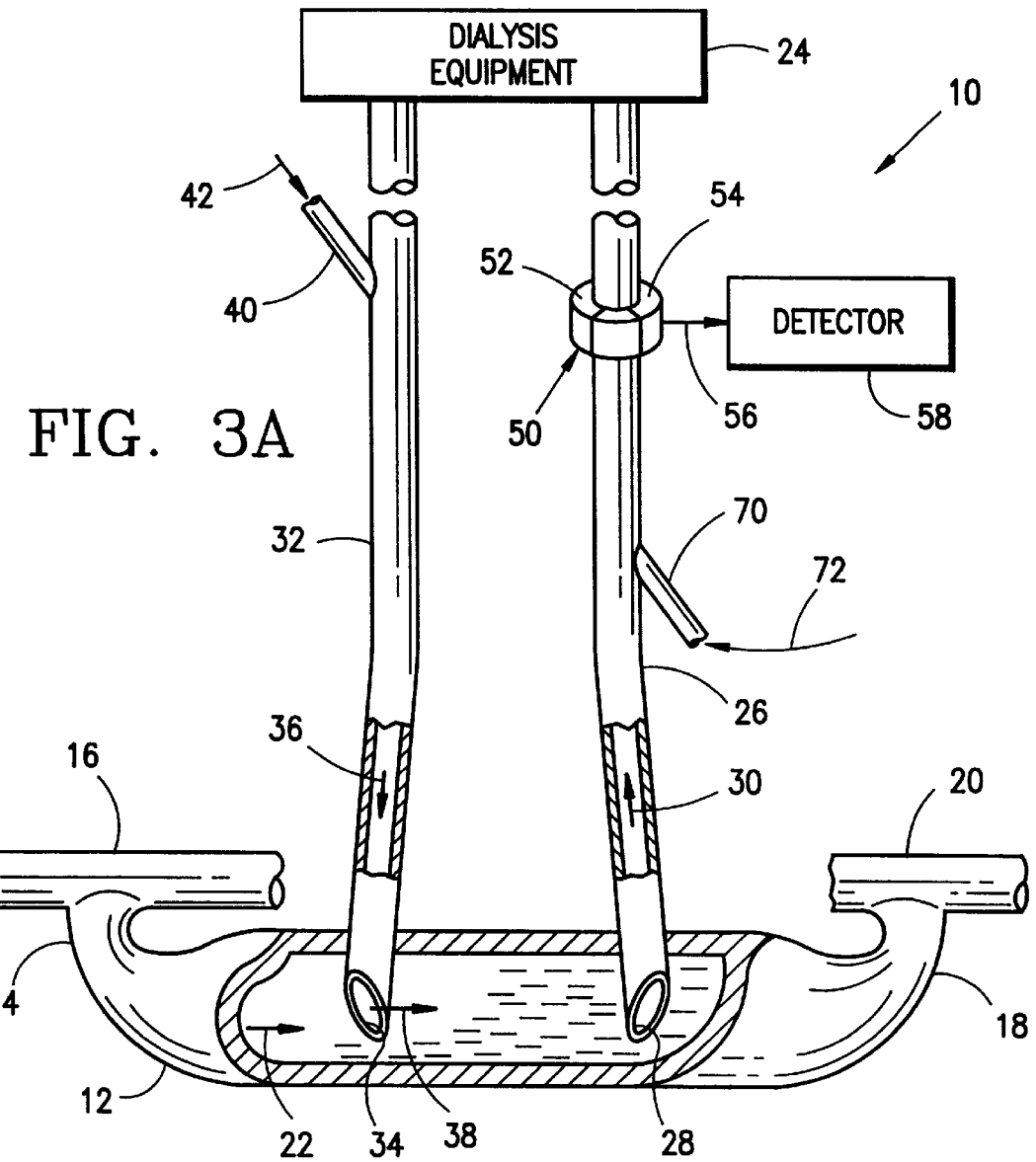
FIG. 3A is a second modification of FIG. 1A, adding an injection port in the arterial tube, upstream of the arterial sensor.
Figure 3B:
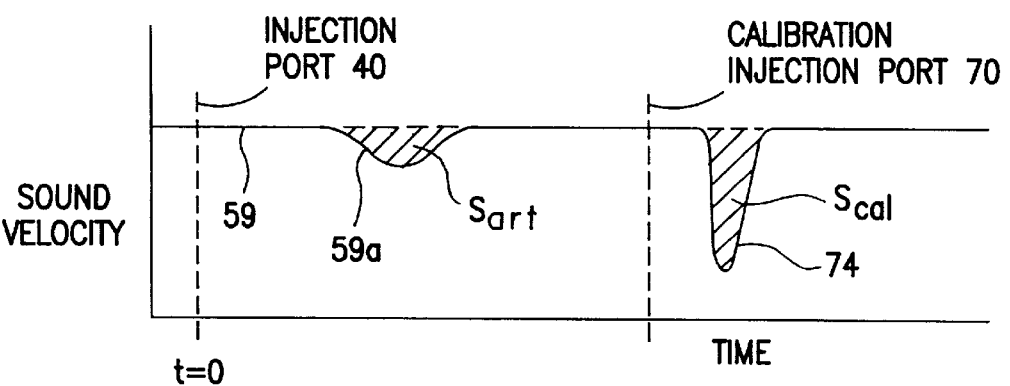
FIG. 3B illustrates a dilution curve for the device of FIG. 3A.

Referring to FIG. 3, another modification of the invention is shown which is the same as FIG. 1 but with the addition of an injection port 70 in the arterial line 26 for injecting a calibration indicator material, as shown by line 72. Injection port 70 is located upstream of the sensor 50 so that the indicator material 72 is mixed with all of the blood flow in line 26. The injection of the calibration indicator material in port 70 produces a corresponding dilution curve as illustrated at 74 in FIG. 3A in accordance with the change in sound velocity in the blood as sensed by sensor 50. This dilution curve is recorded by detector 58, which determines the blood flow $Q_{dial}$ in line 26 from the area $S_{cal}$ under curve 74 and from the known volume $V_{cal}$ of indicator material 72 in accordance with Equation 4. This blood flow $Q_{dial}$ is then subtracted from the sum of flows calculated in accordance with the embodiment of FIG. 1 to increase the accuracy of the shunt blood flow measurement in accordance with Equation 6.

Figure 4:
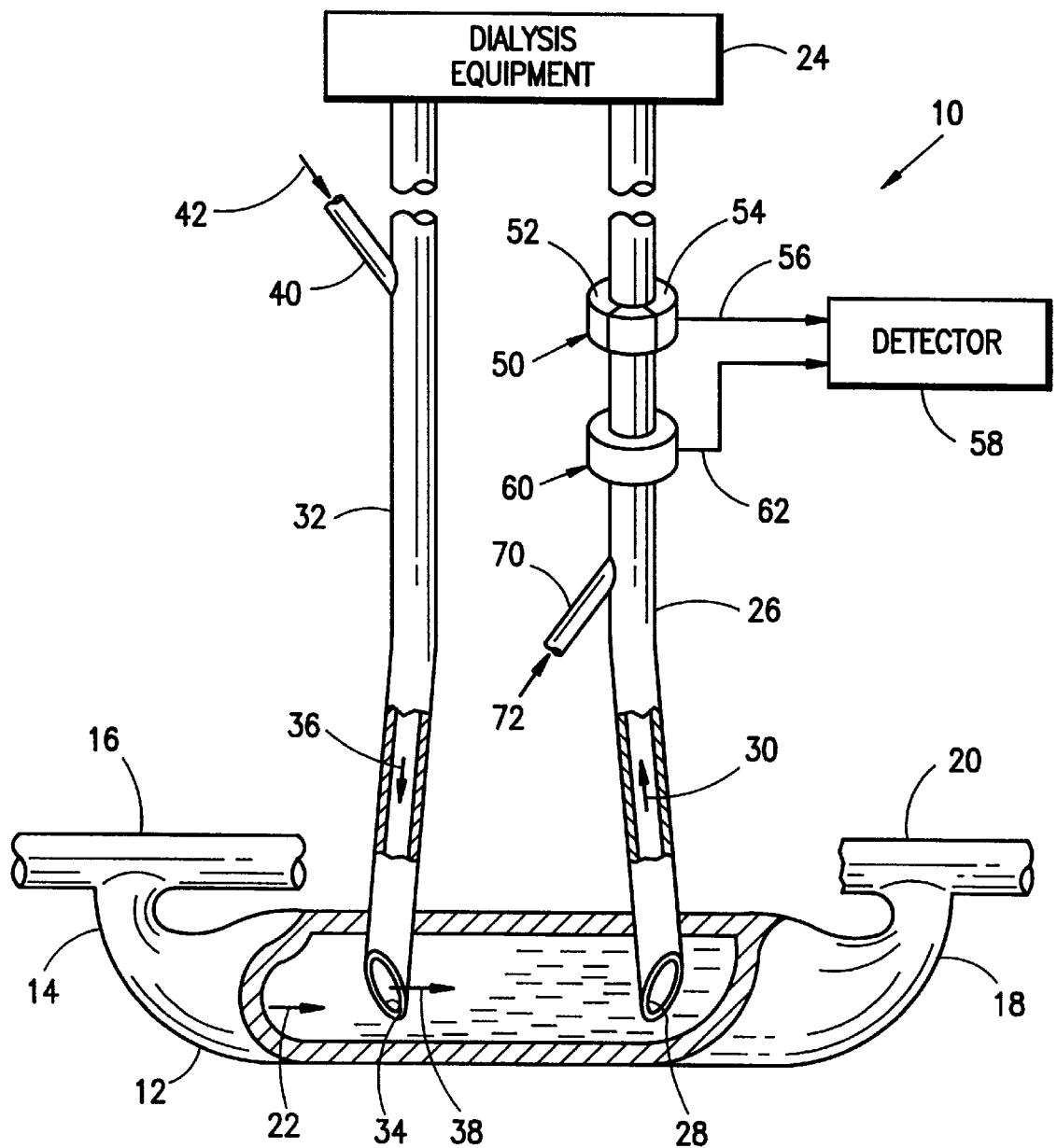
FIG. 4 is a third modification of FIG. 1A, adding a second arterial sensor of the type illustrated in FIG. 2 to the device of FIG. 3.

Referring to FIG. 4, another modification of the embodiment of FIG. 1 is illustrated which includes all of the measurements of the embodiments of FIGS. 1, 2, and 3. Thus, the embodiment of FIG. 4 includes (a) sensor 50 with a sound source 52 and a sound receiver 54 supplying signals on line 56 to detector 58, (b) a blood flow sensor 60 connected by way of line 62 to detector 58, and (c) a calibration injection port 70 for receiving calibration indicator material 72. The output signal on line 62 is for measuring the dialysis blood flow $Q_{dial}$. The indicator 72 is a calibration injection, as described above, and relative changes of sound velocity related to known blood flow $Q_{dial}$ are measured by sensor 50. The relative changes of sound velocity corresponding to injections made into port 40 of indicator material 42 and into port 70 of the same indicator material 72 are recorded by sensor 50, so that relative changes of sound velocity in arterial line 26 due to these injections can be calculated in detector 58 to obtain an accurate shunt blood flow measurement in accordance with Equation 5.

Figure 5:
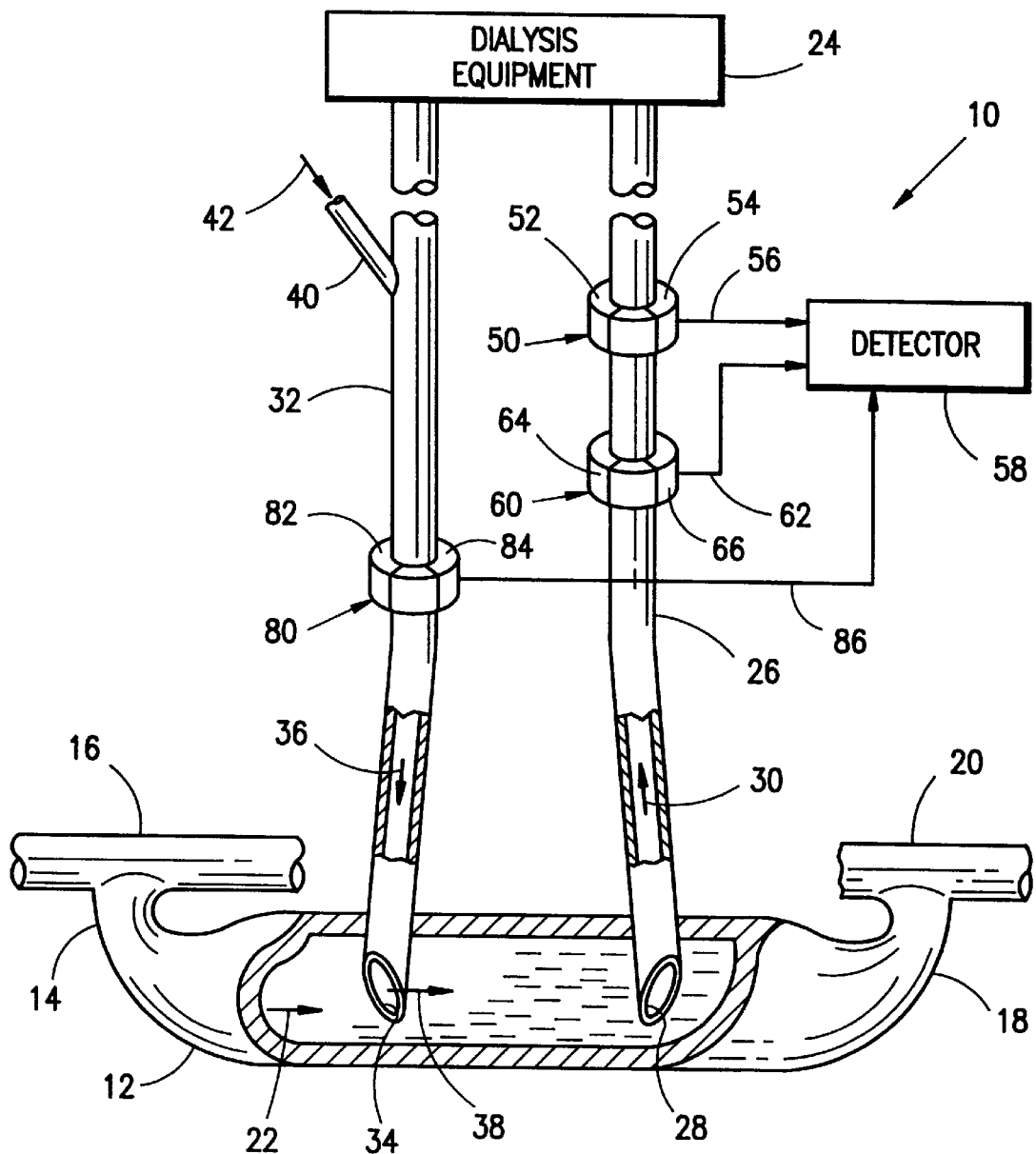
FIG. 5 is a fourth modification of FIG. 1A, incorporating two additional sensors, one for each of the venous and arterial tubes.
Figure 5A:
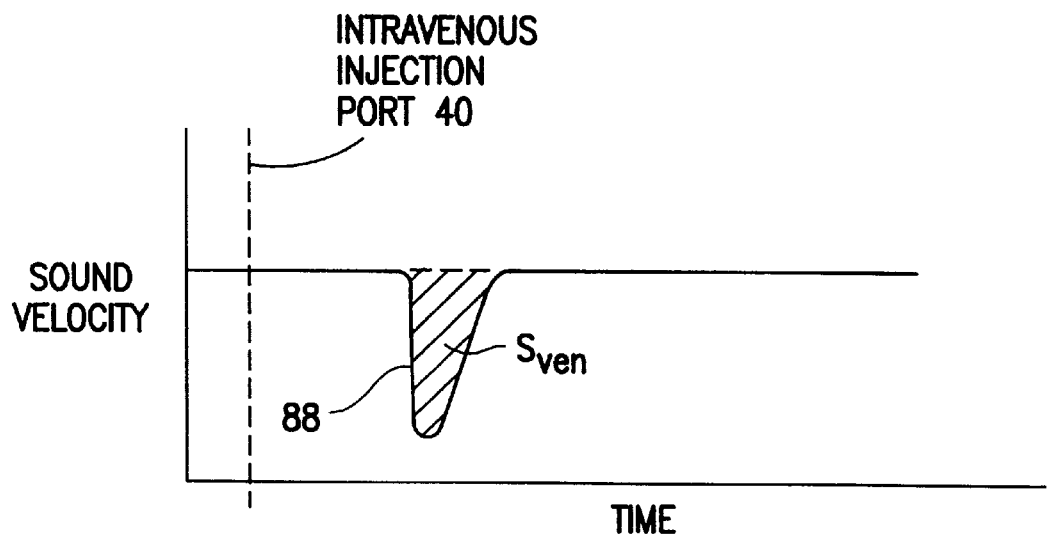
FIG. 5A illustrates a dilution curve for the device of FIG. 5.
Figure 5B:
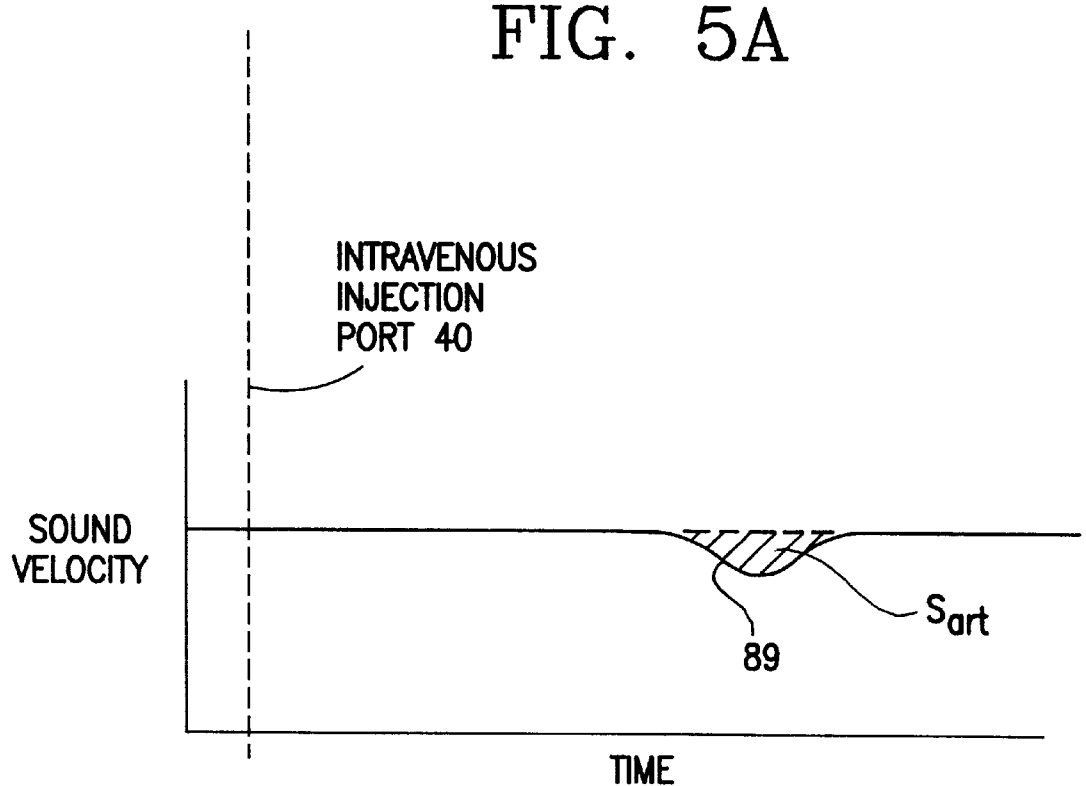
FIG. 5B illustrates a dilution curve for the device of FIG. 5.

Referring to FIG. 5, another modification of the embodiment of FIG. 1 is illustrated which is similar to the embodiment of FIG. 2 but with the addition of a sensor 80 located on the venous line, or tube, 32. Sensor 80 includes a sound transmitter 82 and a sound receiver 84, which produces an output signal on output line 86 which is connected to detector 58. The use of sensor 80 avoids the need for additional calibration injections in arterial line 26. The additional sound velocity source 82 and receiver 84 match the sound velocity source 52 and receiver 54, and sensor 80 is located downstream of the injection port 40 in venous line 32. As a result, all of the indicator material 42 flows through sensor 80, producing dilution curve 88 as shown in FIG. 5A. The injection made in port 40 is mixed only with the blood flow in venous line 32, thus serving to calibrate the sensor 80. The same injection later generates dilution curve 89 in the matching sensor 50 as shown in FIG. 5B after the indicator material passes through the shunt vessel 12, while a portion is recirculated into arterial line 26. The calculation of shunt blood flow $Q_{sh}$ is then made in accordance with Equation 8.

Figure 6:
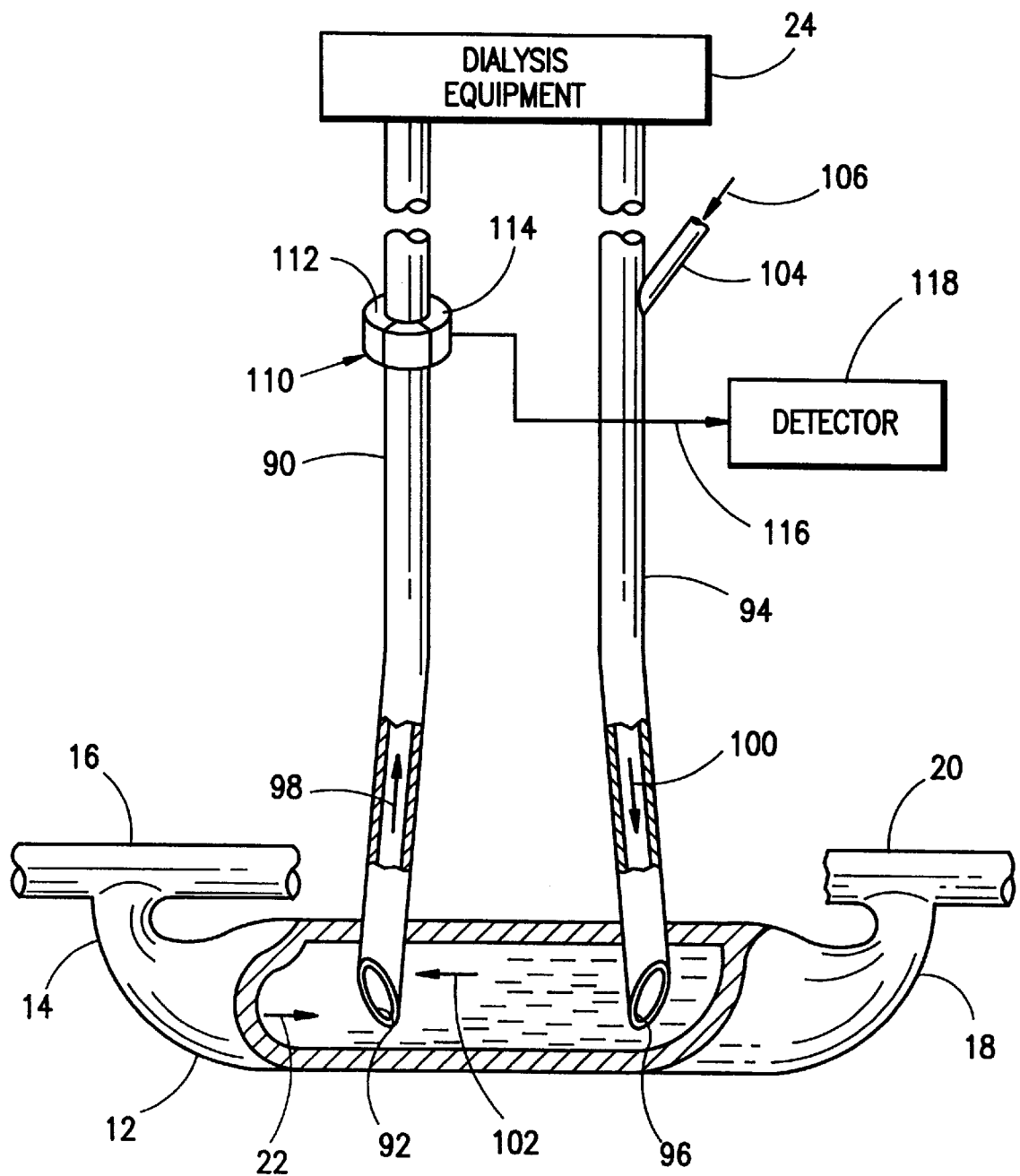
FIG. 6 is a diagrammatic illustration of a second embodiment of the invention, illustrating an arteriovenous shunt connected by way of arterial and venous tubes to a dialyzer, with an arterial tube inlet in the shunt upstream of a venous tube outlet, an injection port in the venous tube, a sensor for the arterial tube, and a calibration port in the arterial tube upstream of the sensor.

Referring to FIG. 6, a second embodiment of the invention is illustrated. This embodiment provides a measurement of undesired recirculation of freshly purified blood while utilizing a "normal" connection of the dialysis equipment lines. Thus, in this embodiment the dialysis equipment 24 is connected to a patient's vascular system by way of shunt 12 and an arterial line 90 leading from inlet 92 to the dialysis equipment. Similarly, the equipment is connected to shunt 12 by venous line 94 which delivers purified blood from the dialysis equipment through outlet 96 in the shunt. The direction of blood flow in arterial line 90 is illustrated by arrow 98, and the direction of blood flow in venous line 94 is illustrated by arrow 100.

Although the outlet 96 is downstream from the inlet 92 in shunt 12, such a "normal" connection can produce undesired recirculation of purified blood, as illustrated by arrow 102. Thus, purified blood can flow upstream in vein 12 and be picked up at inlet 92 for recirculation through the dialysis equipment, such recirculated blood then making up a part of the arterial blood flow 98.

To measure this recirculation, an indicator material having a selected physical property differing from that of the blood is injected into the venous line 94 through an injection port 104. The indicator material, indicated by arrow 106, is preferably a saline solution isotonic with the blood, but having a different physical property from blood. In this embodiment, the different physical property used is sound velocity. The injection of such an indicator dilutes the blood in venous line 94, and if recirculation exists, some of the diluted blood appears in arterial line 90, producing resultant sound velocity changes which are recorded by a sensor 110 having a sound source 112 and a sound receiver 114. The receiver 114 is connected by way of line 116 to a detector 118 of the type described in the previous embodiment. The detector serves as a measuring and evaluating device which records the received signals, calculates the area under the dilution curve which results from the injection of the indicator material, and carries out the calculations prescribed by the equations described above.

An additional calibration injection of indicator material 120, which is the same as the indicator material 106, may be injected by way of a port 122 in arterial line 90, upstream of the sensor 110. Since all of the blood in the arterial line 90, upstream of the sensor 110, passes through the sensor 110, the indicator material injected at 122 is mixed only with this arterial blood flow. The resulting dilution curve recorded by detector 118 permits calibration of the system by calculating the area under the dilution curve and subsequent determination of the recirculation fraction in accordance with Equation 10.

Figure 7:
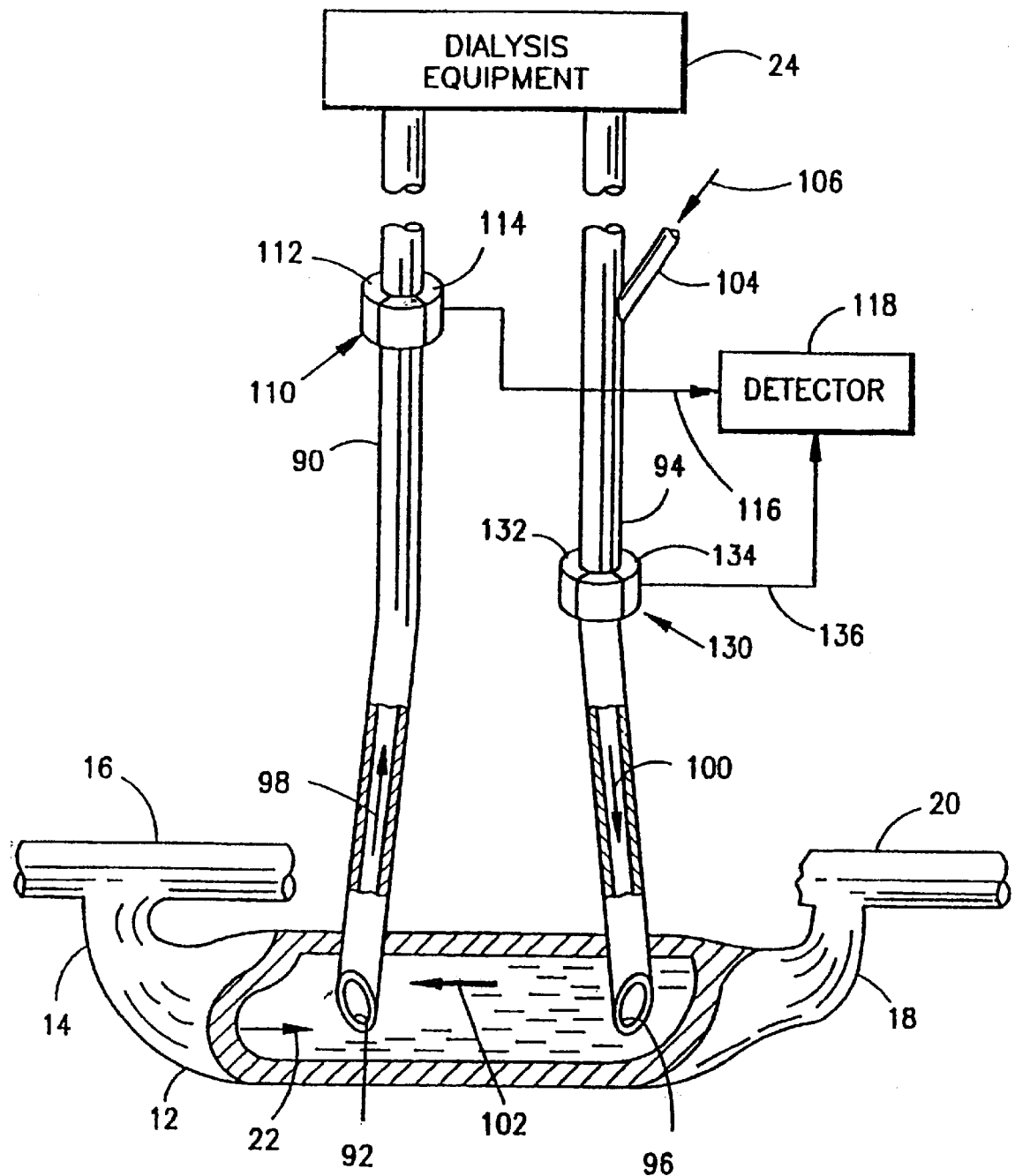
FIG. 7 is a diagrammatic illustration of a modification of the device of FIG. 6, wherein the calibration port of FIG. 6 is replaced by a venous tube sensor downstream of the venous tube injection port.

Referring to FIG. 7, a modified version of the device of FIG. 6 avoids the need for a recalibration injection. In this modification, an additional sensor 130 having a sound velocity source 132 and a sound velocity receiver 134 is provided on the venous line 94. The receiver 134 is connected by way of line 136 to the detector 118. The sensor 130 matches sensor 110 and is located downstream of the injection port 104, so that all of the blood from the dialysis equipment 24, as well as the indicator material 106 injected in port 104, passes through sensor 130. The sensor measures the dilution curve in the arterial blood 100, and the same injection then produces a dilution in the flow 98 through arterial line 90. Sensor 110 detects the indicator material to provide a resulting signal to detector 118 from which the recirculation can be calculated in accordance with Equation 11, as outlined above with respect to the first embodiment and the various modifications thereof described with reference to FIGS. 1–5. The foregoing indicator dilution processes identify access recirculation in the dialysis shunt with a high degree of accuracy.

Figure 8:
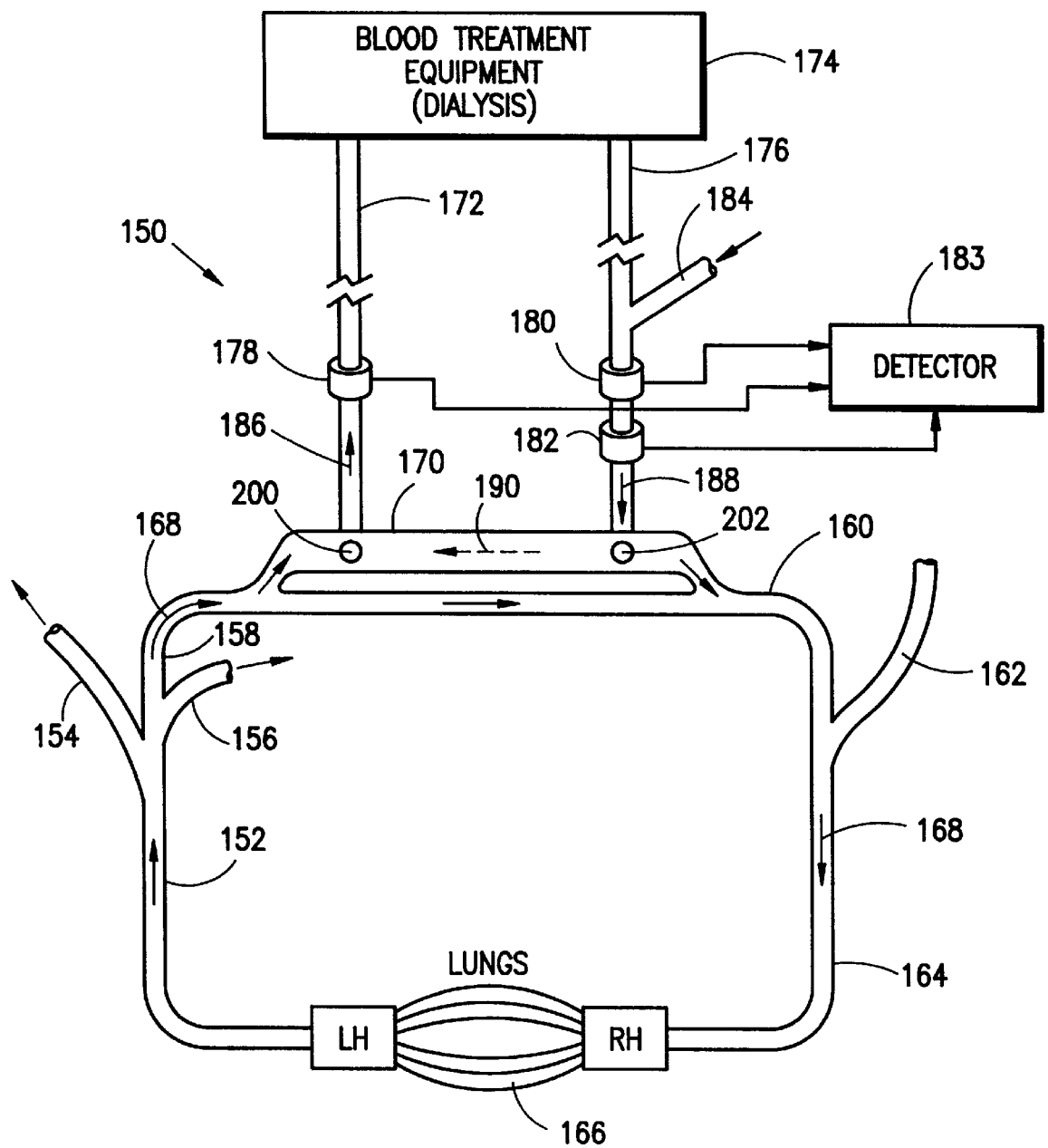
FIG. 8 is a diagrammatic illustration of the two circulation pathways in a cardiovascular circuit and dialysis shunt.

Referring to FIG. 8, there are two pathways by which an indicator can reenter the arterial line of the dialysis equipment. This figure illustrates a dialysis patient's cardiopulmonary circuit, or system 150, which includes a normal circulation pathway including, for example, the left heart LH; arteries 152, 154, 156, 158; veins 160, 162, 164; the right heart RH; and the lungs 166. Blood flows in this pathways in the direction indicated by arrows 168. A dialysis access shunt 170, such as that described with respect to FIG. 1, is connected in artery 158, in the conventional manner, and includes, for example, an arterial line 172 leading to dialysis equipment 174 and venous line 176 leading from equipment 174 to vein 160. The lines 172 and 174 carry dilution sensors 178 and 180, respectively, while line 172 carries a flow sensor 182, with the sensors being connected to suitable detector circuits 183 for receiving and recording sensor output signals. Venous line 176 also includes an injection port or site 184.

Blood which passes through dialyzer 174 flows upwardly in line 172 and downwardly in line 176, as indicated by flow arrows 186 and 188, respectively. Direct circulating flow between venous line 176 and arterial line 172 occurs in the shunt 170 as illustrated by arrow 190, and flow through this pathway may be termed shunt or access recirculation.

When an indicator is introduced upstream of dilution sensor 180, for instance into venous line 176 at port, 184, some of the indicator is carried to the arterial line 172 by the shunt recirculation flow 190 for measurement by arterial sensor 178, as discussed above. However, some of the indicator flows from line 176 indirectly to line 172 by way of the patient's normal cardiopulmonary pathway, flowing through vein 168, the patient's heart and lungs, and into artery 158, where it is delivered to arterial line 172 and detected by arterial sensor 178. If the direct (shunt) recirculation of the indicator is not separated from the indirect cardiopulmonary recirculation (CPR), a false positive diagnosis of shunt recirculation can be obtained in cases where only CPR is present.

The recirculation through the normal cardiopulmonary pathway always exists, for it is a functional parameter of the heart and not a malfunctioning parameter of the dialysis process. Therefore, it is of primary importance for correct diagnosis of the adequacy of the dialysis to separate CPR from shunt recirculation. The indicator dilution curve recorded by the arterial line sensor 178 upon the introduction of a venous line indicator bolus must be further diagnosed to separate CPR from shunt recirculation. Two methods, and the combination of these two methods, for achieving this separation are described below. The first method is directed to a process for analyzing the relationship of the expected appearance time of a waveform that is produced by an indicator at a sensor due to shunt recirculation (if it exists) and the observed appearance time of a waveform produced by a measurement of the indicator at a sensor. Shunt recirculation generally appears before CPR. The second method involves an analysis of the waveforms produced by the indicator measurement: shunt recirculation waveforms have a pulsatile shape, whereas CPR waveforms have a smooth curve and are longer in duration. These two methods can be combined to provide improved separation of the two types of recirculation.

Method 1

In accordance with the first method, an analysis of the expected time of arrival of an indicator at arterial sensor 178 due to shunt recirculation 190 is based on an accurate detection and recording of a venous dilution bolus by venous dilution sensor 180 and arterial dilution sensor 178 after introduction of the bolus into venous access line 176 at port 184. The rate of blood flow (Qb) in the dialysis lines is measured at sensor 182, and the travel time (Tv) between the venous sensor 180 and the shunt 170 at location 202, and the travel time (Ta) between the shunt 170 at location 200 and the arterial sensor 178 are determined by:

$$Tv = \frac{Vv}{Qb} \quad \text{(Eq. 12)}$$

and $$Ta = \frac{Va}{Qb}, \quad \text{(Eq. 13)}$$

where Vv is the volume of blood in the venous line, or tube, between the venous sensor 180 and shunt 170 and Va is the volume of blood in the arterial line, or tube, 172 between shunt 170 and arterial sensor 178.

The time (Tav) required for the indicator to travel the length of the shunt between the connection of the arterial line 172 to the shunt, indicated at 200, and the connection of the venous line 176 to the shunt, indicated at 202, is a ratio of the volume (Vav) of blood in the shunt to the value of the recirculation flow (Qrec):

$$Tav = \frac{Vav}{Qrec}. \quad \text{(Eq. 14)}$$

The time (Tr) required for the indicator to travel from the venous sensor 180 to the arterial sensor 178, for the case of shunt recirculation, can be calculated as follows:

$$Tr = Tv + Ta + Tav \quad \text{(Eq. 15)}$$

which may be expressed as:

$$Tr = \frac{Vv + Va + \frac{Vav}{R}}{Qb} \quad \text{(Eq. 16)}$$

where R=Qrec/Qb and is the shunt recirculation ratio.

Figure 9A:
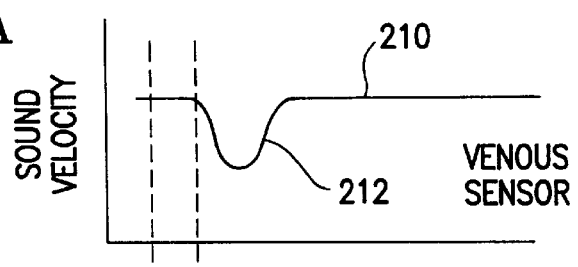
FIG. 9A illustrates the shape of waveforms produced at the venous dilution sensor by shunt recirculation.
Figure 9B:
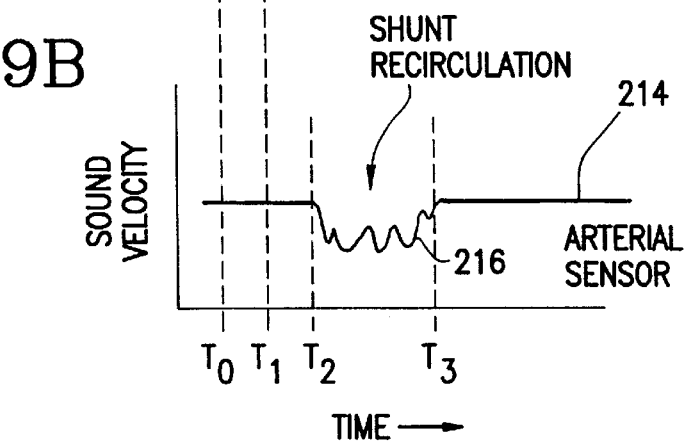
FIG. 9B illustrates the pulsatile shape of waveforms produced at the arterial dilution sensor by shunt recirculation.

Referring to FIGS. 9A–9B, a graph of measured sound velocity in blood of an indicator versus elapsed time from the injection of the indicator at port 184 is shown. Curve 210 represents the output of venous sensor 180 as measured and recorded at detector 183, showing at 212 the change in sound velocity beginning at time $T_1$ due to the passage of a bolus injected at time $T_0$. Curve 214 indicates at 216 the change in sound velocity caused by the presence of the indicator at arterial sensor 178 due to shunt recirculation. As illustrated, the waveform 216 starts at time $T_2$ and ends at time $T_3$, having a pulsatile shape which is a characteristic of shunt recirculation.

Figure 10A:
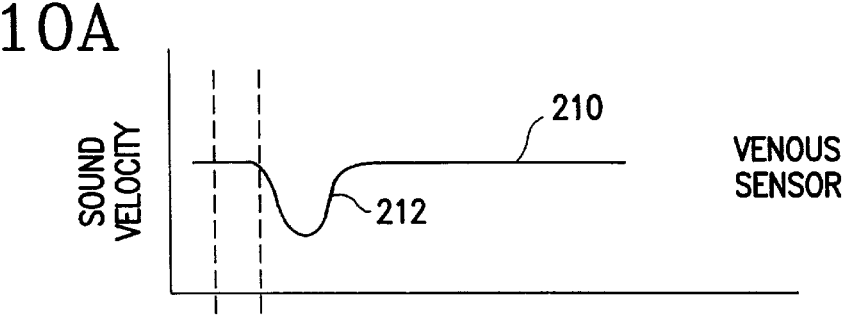
FIG. 10A illustrates the smooth shape of waveforms produced at the venous sensor by cardiopulmonary recirculation.
Figure 10B:
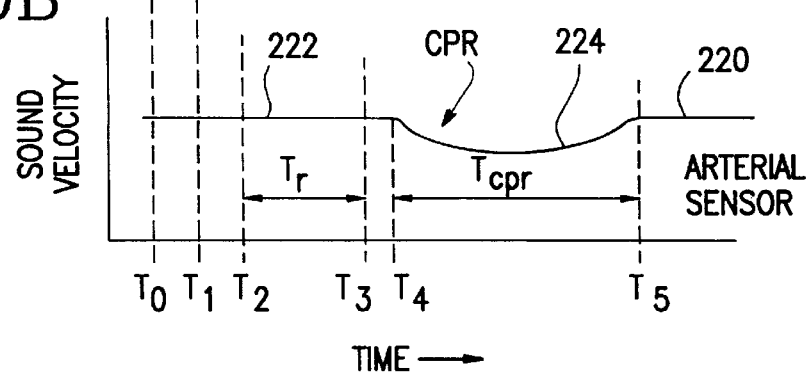
FIG. 10B illustrates the smooth shape of waveforms produced at the arterial sensor by cardiopulmonary recirculation.

Referring to FIG. 10, the passage of the bolus past venous sensor 180 as described with respect to FIG. 9 is shown and also includes curve 210. FIG. 10 illustrates at curve 220 the time relationship between the indicator which travels through the shunt recirculation path and that which travels through the cardiopulmonary recirculation path. The effect of this shunt recirculation indicator on sound velocity measurements at arterial sensor 178 occurs at time $T_2$ to $T_3$, which defines a time window Tr, indicated at 222 on curve 220, during which an indicator due to shunt recirculation can be expected. At a later time $T_4$ the indicator which travels through the CPR pathway reaches the sensor 178, which then measures a change in sound velocity as indicated at 224 on curve 220. The portion 224 of the curve is more rounded than curve portion 216, and extends over the time period $T_4$–$T_5$ which is of longer duration than curve 216. The time period $T_4$–$T_5$ defines a time window Tcpr during which an indicator due to CPR can be expected. The time window Tcpr can, by analogy, be written:

$$Tcpr = Tv + Ta + Tco \quad \text{(Eq. 17)}$$

where $$T_{CO} = \frac{Vrh + Vlh + Vl}{CO} \quad \text{(Eq. 18)}$$

where Vrh is the blood volume in the right heart, Vl is the blood volume in the lungs, Vlh is the blood volume in the left heart, and CO is cardiac output.

Comparing Eq. 15 and Eq. 17 illustrates that the time difference between Tav+(Vav/R)/Qab and Tco=(Vrh+Vlh+Vl)/CO can be used to separate shunt recirculation from cardiopulmonary recirculation in the indicator dilution signal produced by arterial sensor 178. Based on thousands of clinical measurements it was found that the time windows for shunt recirculation and for cardiopulmonary recirculation are different. It was found that shunt recirculation appears (Vav/R/Qb) within 1–8 seconds (after adjustments for Ta and Tv) and cardiopulmonary recirculation appears (Vrh+Vlh+Vl)/CO) within 6–20 seconds (after adjustments for Ta and Tv).

In extensive patient studies, a 2–3 second overlap between shunt recirculation and CPR was observed in only 2% of the data. This 2% error in diagnosis can be further reduced by combining the foregoing Method 1 with the following Method 2.

Method 2

In Method 2, the pulsatility of the waveform obtained from indicator recirculation measurements is analyzed. Shunt recirculation flow has two pulsatile components: pulsatilities in the shunt flow due to the cardiac cycle, and the pulsatilities due to the dialysis roller pump. As a consequence, the indicator concentration in the shunt recirculation bolus and the consequent waveform produced by measurement of this concentration is very pulsatile. During the systolic part of the cardiac cycle, the access line often has sufficient flow to supply the dialysis equipment without shunt recirculation, while during the diastolic part of the cardiac cycle, shunt recirculation is severe. Superimposed on this are the pulsatile fluctuations of the roller pump, through which the delivery of the indicator into the access line (and thus the concentration of indicator) is modulated. In contrast to this, the measurement of the indicator that passes through the cardiopulmonary pathways results in a smooth curve for the indicator since the indicator is well mixed in the blood stream after passing through both sides of the heart. Passage through the cardiopulmonary pathway also makes the CPR dilution curve longer in time than the shunt recirculation, while the duration of the shunt recirculation bolus mimics the duration of the bolus introduced in the venous line. The CPR curve is more elongated because the bolus is diluted in the heart chamber with the other components of the patient's flow, and only gradually released with each heart beat. Therefore, a wave form analysis algorithm can be used to analyze the shape of the indicator dilution curve registered by the arterial sensor 178 to distinguish between shunt recirculation and CPR.

Method 3

To improve the accuracy of the measurements, the procedure outlined for Method 1 is combined with that of Method 2. Preferably, a time analysis of the waveforms is first performed, as described in Method 1. In case there is any ambiguity, the wave form analysis of Method 2 is then performed, as by the use of a correlation analysis. The blood volume in the arterial and venous tubing between the sensors and the shunt is measured to calculate Ta and Tv using the measurement of Qb (Eqs. 12 and 13). After the venous sensor 180 records an incoming dilution bolus and the arterial sensor 178 records an arterial bolus, a regression analysis is performed to find the time lag between the curves. From this time, the value (Ta+Tv) is subtracted. Then, if the remaining time is less than 6 seconds, the measured arterial bolus is considered shunt recirculation and the ratio of the areas of arterial and venous curves represents the percentage recirculation as shown in Eq. 11. If the remaining time is more than 8 seconds, then it is considered that there is no shunt recirculation. If the time remaining is between 6 and 8 seconds, then the pulsatility of the curve is calculated, using a comparison of the average values of maximum and minimum deviation from the curve.

Figure 11A:
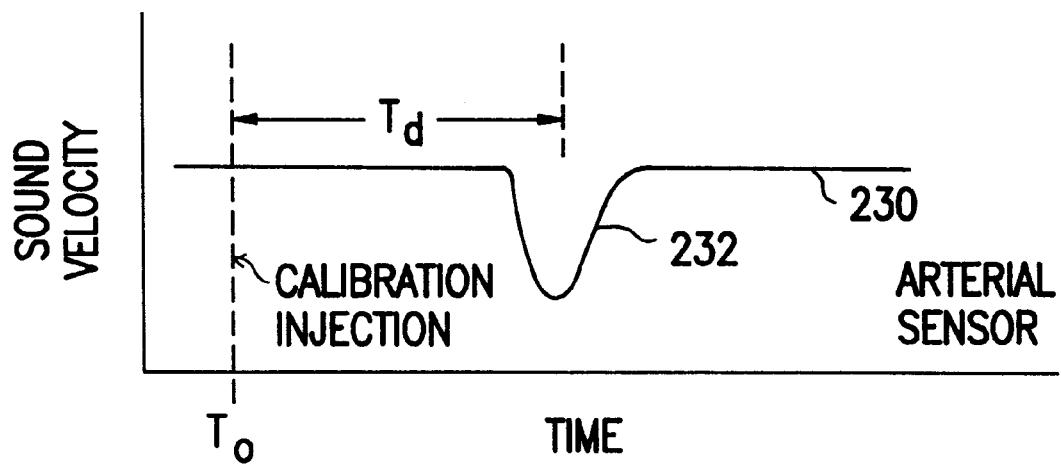
FIG. 11A shows the dilution curve produced at a single arterial sensor for a calibration injection.

Modifying the measuring apparatus of FIG. 8, a single arterial sensor 110 is used as described with respect to the device of FIG. 6. In that arrangement, a calibration injection is provided in the arterial line at port 122, producing the curve 230 at sensor 110 as illustrated in FIG. 11A. The calibration injection at 122 results in the change in curve 230 illustrated at 232, so that by measuring the time $T_d$ between the calibration injection and the curve 232, an estimate can be made of the times Ta and Tv that the indicator travels in the tubes, or lines, 172 and 176. This avoids the need for a flow sensor (Eq. 12 and 13).

Figure 11B:
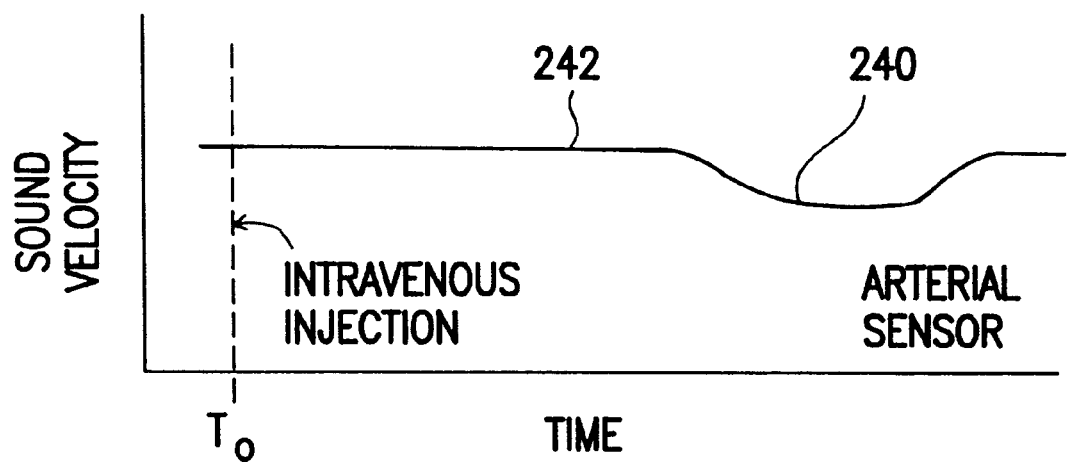
FIG. 11B shows the dilution curve produced by the single arterial sensor used for the curve of FIG. 11A for an intravenous injection.

After the calibration injection, an intravenous injection of an indicator in the venous line may be made, recording the time of the injection either by a suitable sensor or manually, such as by pressing a start button on a detector circuit timer or on a computer which records the measured waveforms. This establishes the start of the time windows for the indicator measurements, allowing accurate measurement of the change in sound velocity (or other indicator parameter) as indicated at 240 for a CPR measurement on curve 242 obtained at sensor 110 and illustrated in FIG. 11B.

It is noted that if shunt recirculation exists, the actual percentage of recirculation in many instances is of secondary importance. As an example, if the access line flow is 300 ml/min, there is approximately 100 ml/min recirculation (33%) if the dialysis pump is turned up to 400 ml/min pump flow, but there is zero % recirculation if the pump is turned down to 250 ml/min. Therefore, the present invention is capable of providing accurate measurements which enable the user to determine whether access recirculation exists at a pump flow of a selected number of ml/min.

A disadvantage of the prior at technology is that reversing the lines is actually done by disconnecting the blood lines from the dialysis tubing and reconnecting them in reversed position. In order to change the direction of blood flow by reversing the pump flow instead of physically reversing the lines requires redesigning the blood lines and the bubble trap systems due to the danger of introducing air into the patient's circulatory system. The embodiments described below avoid the problems of hemodialysis line reversal during measurement of blood flow.

Figure 12:
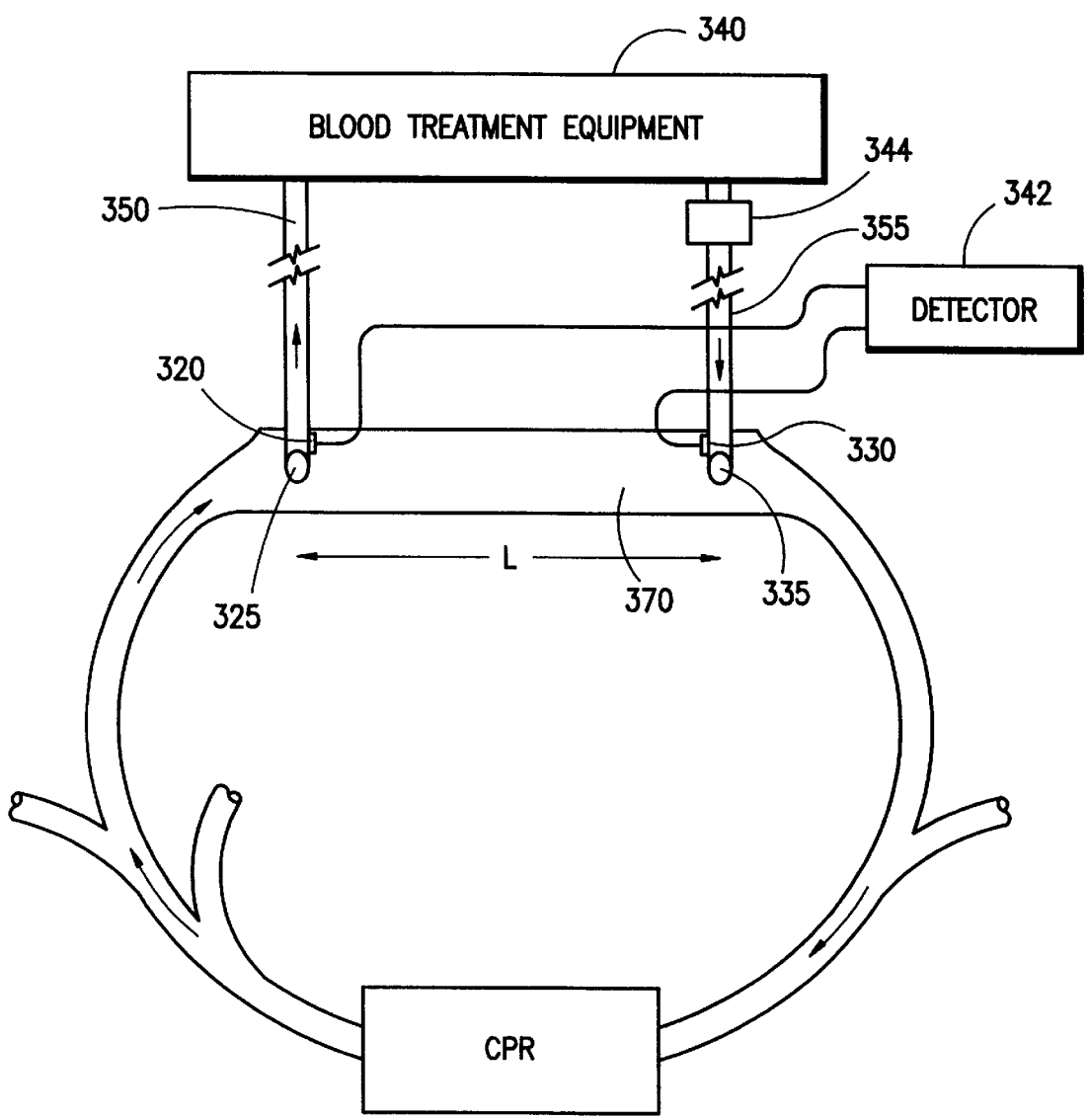
FIG. 12 is a diagrammatic illustration of the two circulation pathways in a cardiovascular circuit and dialysis shunt, showing alternate locations of sensors.

Referring to FIG. 12, a cardiovascular-hemodialysis circulating system is shown which includes a cardiovascular portion and a hemodialysis portion. Blood flow $Q_{sh}$ in a shunt 370 can be calculated based on the time that it takes blood to move downstream in the shunt 370 from a first sensor 320 to a second sensor 330:

$$Q_{sh} = V \times S, \quad \text{(Eq. 19)}$$

where S is the average cross-section area of the vascular shunt 370 between the sensors 320, 330 and V is the average line velocity of the blood in the shunt 370 between the sensors 320, 330. Equation (19) can be rewritten by substituting L/T for V as:

$$Q_{sh} = \left(\frac{L}{T}\right) \times S, \quad \text{(Eq. 20)}$$

where L is the distance between the sensors 320, 330 and T is the average time that blood travels this distance. Since the vast majority of shunts installed in the United States are of standard dimensions, typically 4 mm or 6 mm in diameter, the average cross-section area of shunt 370 is readily determined.

In the normal line position of hemodialysis lines, i.e., when the arterial line bringing blood to the dialysis unit draws blood from the shunt upstream of the location where the venous line returns dialyzed blood to the shunt, the sensors 320, 330 are located on hemodialysis needles 325, 335 or the needles themselves become electrical electrodes or electrical sensors. Sensors 320, 330 are connected to a detector 342 which in turn is connected to an evaluating device (not shown) such as a microprocessor or computer. If a hemodialysis pump within blood treatment equipment 340 is on with a rate of blood line flow $Q_{b1}$, some of the blood normally flowing through shunt 370 is diverted through blood treatment equipment 340. The flow in the shunt between needles 325, 335 is:

$$Q_{sh} - Q_{b1} = \left(\frac{L}{T_1}\right) \times S, \quad \text{(Eq. 21)}$$

where $T_1$ is the time it takes for blood to travel between the sensors 320, 330 at flow rate $Q_{b1}$. Flow rate $Q_{b1}$ is measured by a flow sensor 344.

If the rate of flow is changed, such as by making the pump operate at a faster or slower speed, the flow in the shunt is then characterized as:

$$Q_{sh} - Q_{b2} = \left(\frac{L}{T_2}\right) \times S, \quad \text{(Eq. 22)}$$

where $T_2$ is the time it takes for blood to travel between the sensors 320, 330 at the different flow rate $Q_{b2}$.

The ratio of Equation 21 to Equation 22 is $$\frac{Q_{sh} - Q_{b1}}{Q_{sh} - Q_{b2}} = \frac{L/T_1 \times S}{L/T_2 \times S}. \quad \text{(Eq. 23)}$$

Solving for Qsh, we obtain $$Q_{sh} = \left(\frac{Q_{b1} - Q_{b2}(T_2/T_1)}{1 - T_2/T_1}\right). \quad \text{(Eq. 24)}$$

This formula is independent of L (the distance between the needles) and S (the average cross section area between the needles). If flow rate $Q_{b1}$ is greater than flow rate $Q_{b2}$, time T2 is less than time T1. That is, an increased rate of blood line $Q_{b1}$ flow results in a decreased shunt flow and an increased T1. Decreasing the blood line flow rate to $Q_{b2}$ results in an increased shunt flow and a decreased T2.

After the indicator enters the shunt 370 and moves to the cardiopulmonary system, the pump can be stopped ($Q_{b2}$ set equal to zero) and Eq. 24 is simplified to:

$$Q_{sh} = \left(\frac{Q_{b1}}{1 - T_2/T_1}\right) \quad \text{(Eq. 25)}$$

The indicator that changes a physical property of blood is introduced to measure the travel time of the blood between the sensors (needles). This introduction may be directly into the cardiopulmonary system, but this is difficult to do reliably and consistently. The most convenient way of introducing the indicator is to introduce it through the venous outflow 355, thus changing the blood properties upstream of the venous needle, for example, by injecting a solution of isotonic saline that changes the electrical impedance of blood.

Referring to FIGS. 13A–13B, the indicator travels through the cardiovascular system, and appears on the arterial sensor 320 co-located with the arterial needle 325, as shown by arterial sensor dilution curve 326 in FIG. 13A. The indicator then appears on the venous sensor 330 as shown by venous sensor dilution curve 336 in FIG. 13B. The time shift T1 (for Eq. 24) between the curves in FIGS. 13A and 13B are calculated through transit time differences of the curves or through cross-correlation analysis or other mathematical procedure. Time shift T1 is measured from the same point on each curve, i.e., from the beginning of curve 326 to the beginning of curve 336, from the end of curve 326 to the end of curve 336, from the midpoint of one curve to the midpoint of the other curve, and so forth. The value of T2 for Eq. 24 is calculated from the next intravenous injection at a different Qb2 (a different blood line flow rate) but in analogous manner.

The venous sensor 330 that records the outflow venous indicator is preferably used as a time reference source to record time $t_0$ in FIG. 13A, FIG. 13B, and FIG. 19. This time reference is used to establish a time window of when the indicator bolus is expected at a sensor after traveling through cardiopulmonary system. The time reference is also used to determine if a patient has shunt recirculation, since the indicator released through venous outflow line 355 is quickly recorded by the arterial sensor 320 before the indicator travels through the cardiopulmonary system; the short time between the signal from venous sensor 330 and the signal from arterial sensor 320 helps to identify access recirculation.

Referring to FIGS. 14A–14B, the sensors may use any physiological changes that occur in the body in place of the indicator. For example, fluctuation in the level of hemoglobin due to the breathing conditions can be used. Other types of body pulsations causing a temporary change in the physical property of the blood can also be used. See, for example, D. Schneditz et al., "Methods in Clinical Hemorheology: The Continuous Measurement of Arterial Blood Density and Blood Sound Speed In Man", BIORHEOLOGY, 27; pp. 895–902, 1990, incorporated herein by reference. In this case there is no need in any indicator introduction since identifiable curves found using standard cross-correlation techniques act as the indicator. "Indicator" as used in the disclosure and claims includes such identifiable curves. The value of T1 and T2 may be calculated from recording these physiological events at different blood line flow rates.

Referring to FIGS. 15A–15C, another way to calculate T1 and T2 during the single indicator pass is by changing Qb or even stopping the pump during the time the dilution curve passes both sensors. The first part of the curves during the period t1–t2, when blood line flow is $Q_{b1}$, gives time T1, while the second part of the curves in the period t3–t4, when blood line flow is $Q_{b2}$, gives the value for time T2. In both cases, the shunt flow can be calculated by measuring the blood line flow Qb. Time t1 is specified as being during flow rate $Q_{b1}$ before arterial sensor dilution curve 381, and preferably at the beginning of curve 381. Time t2 is also during flow rate $Q_{b1}$, and is at a time when curve 381 overlaps with venous sensor dilution curve 382. Time t3 is preferably shortly after the flow rate is changed to $Q_{b2}$, as long as curves 381 and 382 continue to overlap. Time t4 is also at flow rate $Q_{b2}$ after the indicator passes the arterial and venous sensors. Since the ratio T2/T1 is used, the exact times of times t1, t2, t3, and t4 are not important as long as the conditions just described are met.

Figure 16:
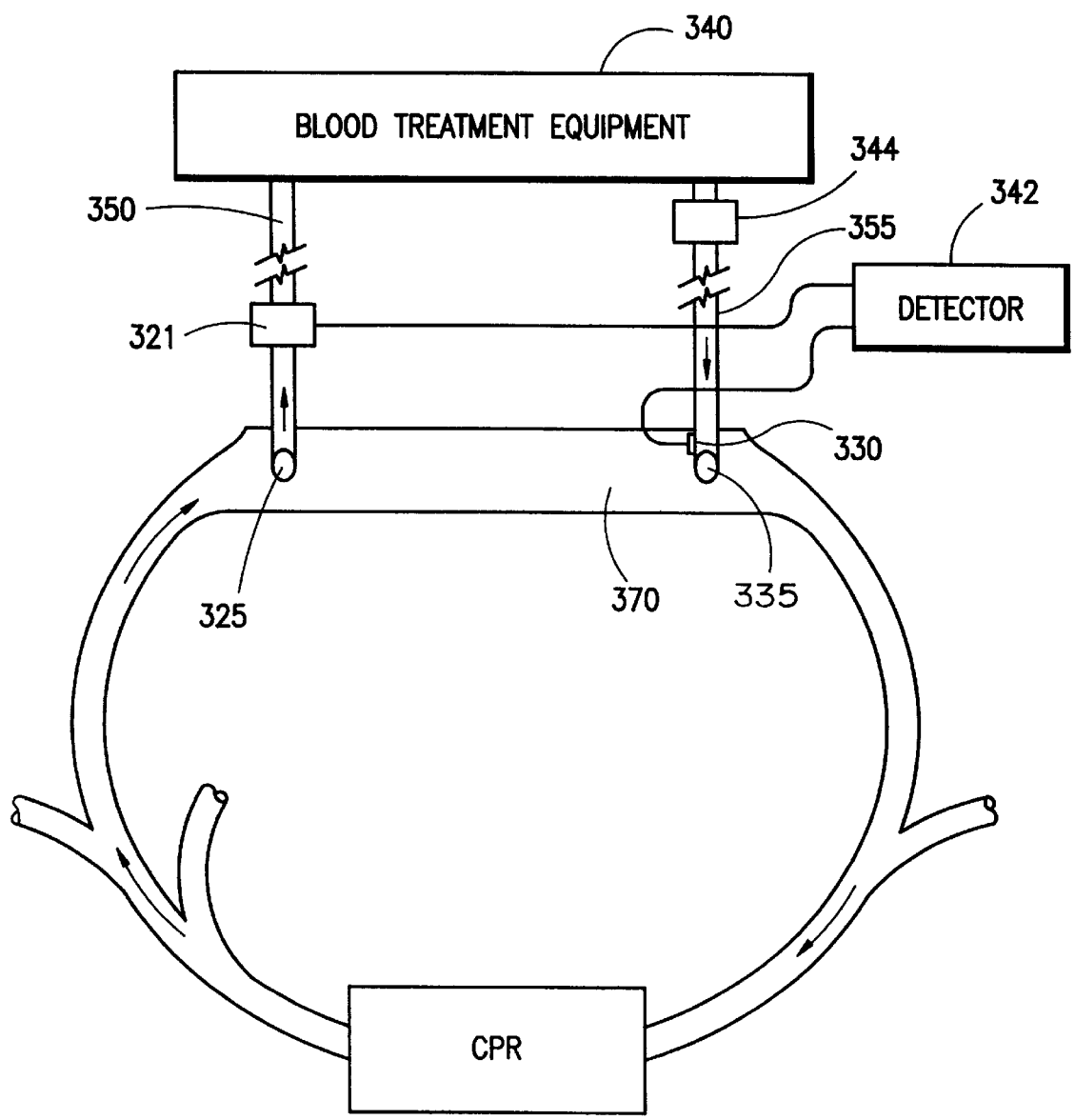
FIG. 16 is a diagrammatic illustration of the two circulation pathways in a cardiovascular circuit and dialysis shunt, with the arterial sensor located within the hemodialysis system.

Referring to FIG. 16, in another embodiment an arterial sensor 321 is located within the hemodialysis system, for example, on arterial inflow line 350. When $Q_{b1}$ is changed to $Q_{b2}$, there is an additional adjustment for the time delay in arterial inflow line due to the additional tubing volume Va between the shunt at needle 325 and arterial sensor 321. This is represented by the following equation:

$$Q_{sh} = \left(\frac{Q_{b1} - Q_{b2}(T_2^*/T_1^*)}{1 - T_2^*/T_1^*}\right), \quad \text{(Eq. 26)}$$

where $$T_1^* = T_{m1} + \left(\frac{V_a}{Q_{b1}}\right), T_2^* = T_{m2} + \left(\frac{V_a}{Q_{b2}}\right),$$

$T_{m1}$ is preferably the time between a point on curve 326 of FIG. 13A and a similar point on curve 336 of FIG. 13B, measured at flow rate $Q_{b1}$, and $T_{m2}$ is the time between a point on curve 326 of FIG. 13A and a similar point on curve 336 of FIG. 13B, measured at flow rate $Q_{b2}$. Volume $V_a$ can be determined several ways. As long as the position of arterial sensor 321 is known, volume Va can be determined from the length of extra tubing and the diameter of the tubing, or from a calibrated syringe measuring the actual volume of the extra tubing.

For the embodiments of FIGS. 12–16, the changes of blood properties in the hemodialysis system may be in thermal properties, chemical properties, electrical properties, ultrasound properties, optical properties, changes in density, and the like. The sensors can be modified as necessary to measure any of the changes in the blood properties. The blood properties can be changed in different ways. Introducing an indicator can be done by injection or withdrawal of an indicator in arterial line 350, venous line 355, or in the blood treatment equipment 340. Introducing an indicator can also be done by heating or cooling the blood by externally applied heat or cold. The indicator can also be introduced by the dialysis itself by detecting a change in the blood properties, that is, determining the blood property before and after dialysis, such as by determining the sodium concentration or ultrafiltration or the like.

Figure 17:
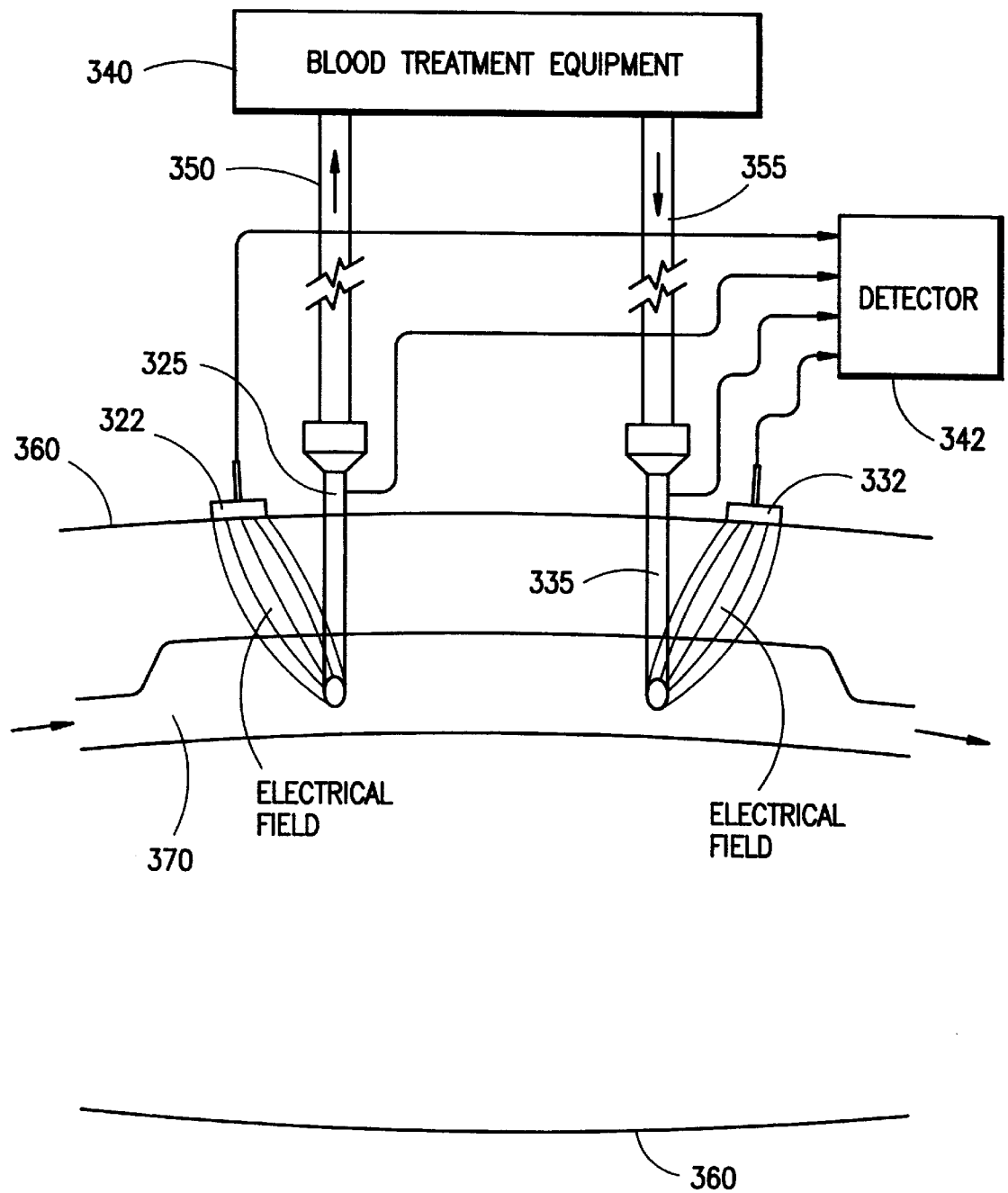
FIG. 17 is a diagrammatic illustration of the two circulation pathways in a cardiovascular circuit and dialysis shunt, with the arterial and venous sensors located on the skin surface of a patient at the site of the arterial and venous hemodialysis needles, respectively.

Referring to FIG. 17, another embodiment includes arterial needle 325 with a corresponding arterial surface electrode 322 and venous needle 335 with a corresponding venous surface electrode 332. An electrical field extends through the skin 360 into shunt 370 and permits the sensor measurements of the indicator to be made.

Figure 18:
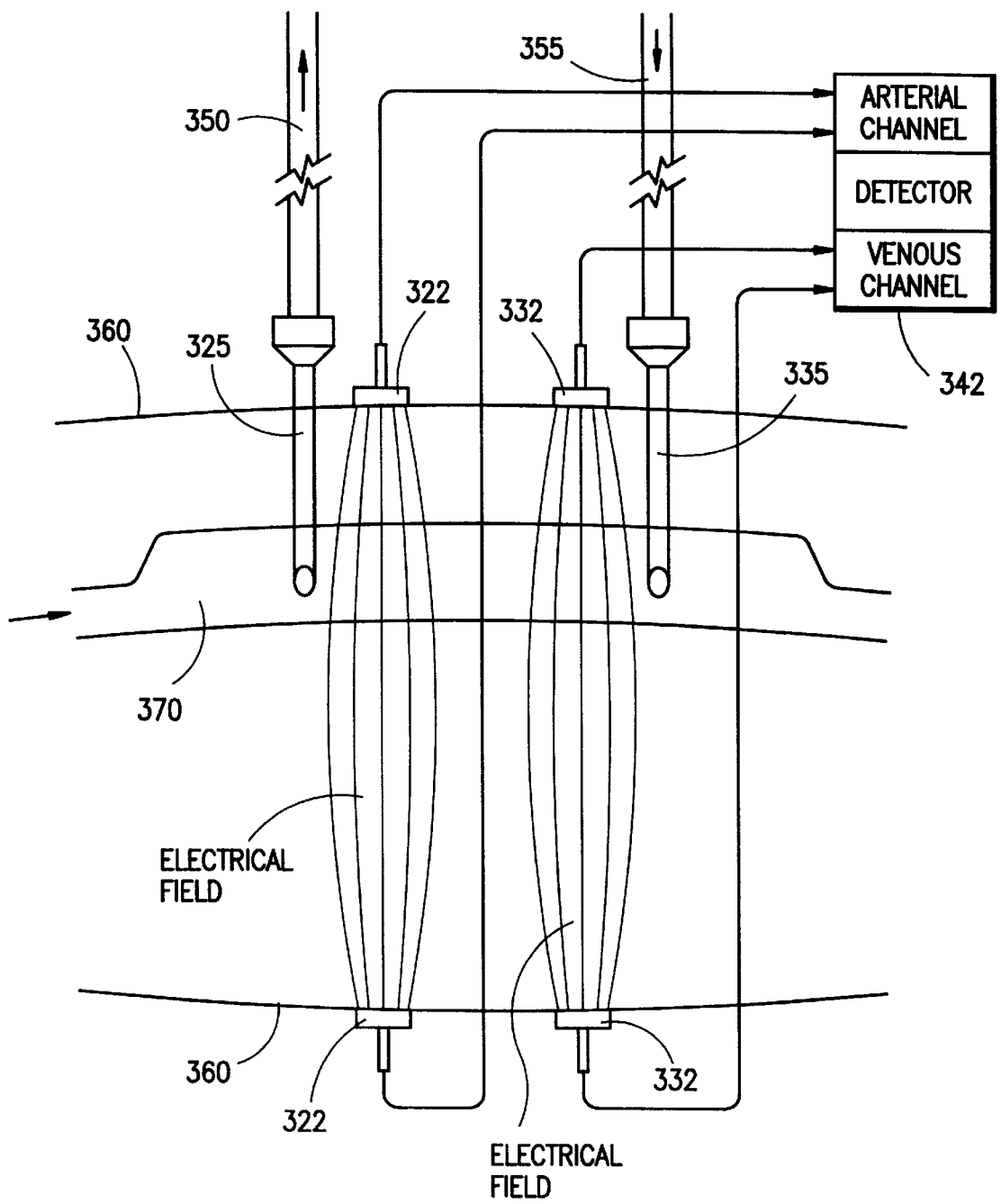
FIG. 18 is a diagrammatic illustration of the two circulation pathways in a cardiovascular circuit and dialysis shunt, with the arterial and venous sensors located on the skin surface of a patient between the locations of the arterial and venous dialysis needles.

Referring to FIG. 18, in a variation of the embodiment of FIG. 17, the dilution sensors are located on the skin above the shunt precisely positioned to be able to sense the dilution curves between the needles. Since the equations do not require the distance between the sensors to be known, the sensors are not limited in their placement except that they must sense the indicator within the shunt and between the needles. These sensors may be electrical impedance sensors, ultrasound sensors, or the like. The idea of the measurements is the same. The sensors measure electrical impedance between the electrodes 1–2 and 3–4. This impedance includes tissue impedance and impedance of flowing blood. The indicator for example hypersonic saline that have electrical impedance significantly different from the blood is introduced through venous line. By analogy after passing the cardiopulmonary system two dilution curves will be produced that represent electrical impedance changes and Eq. 23 can be used.

Referring momentarily to FIG. 12, a common ground, i.e., no surface electrode, can be used to avoid using skin electrodes. In this case, the electrical impedance is preferably measured through the arterial sensor 320 when the venous sensor 330 is turned off to avoid cross current, and vice versa. Or alternating current devices at high frequency can be used to avoid information loss while recording the dilution curve.

Figures 19A, 19B:
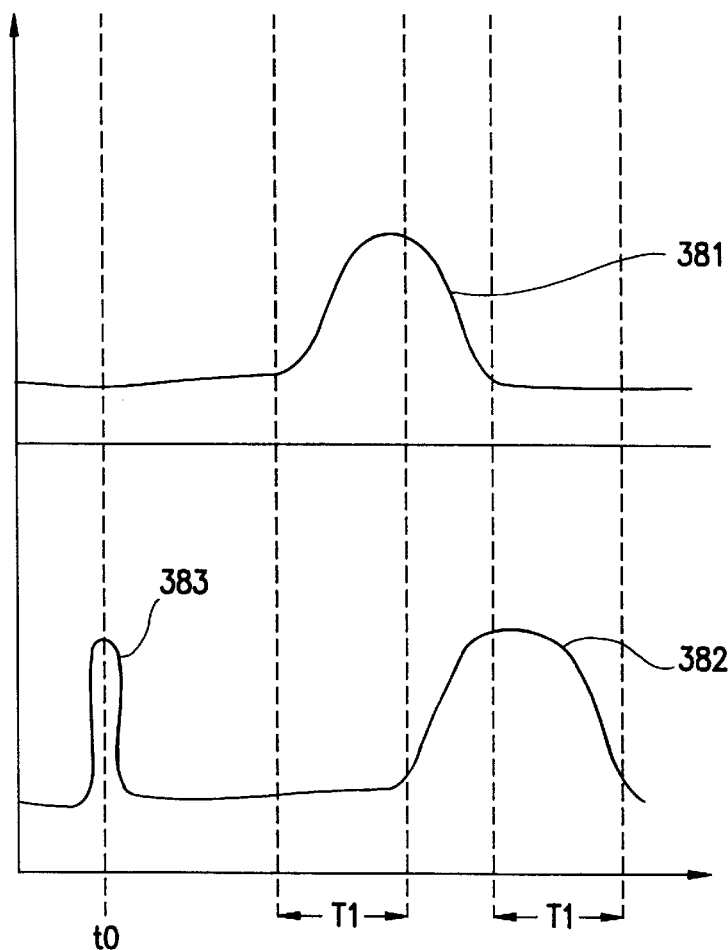
FIG. 19A shows the arterial sensor dilution curve for an introduced indicator.
FIG. 19B shows the venous sensor calibration curve and the venous sensor dilution curve for the introduced indicator producing the curve of FIG. 19A.

Referring to FIGS. 19A–19B, the venous sensor that records the outflow venous bolus can be used as a time reference source. Time T1 is measured from the start of arterial sensor dilution curve 381 to the start of venous sensor dilution curve 382. Time T1 is optionally calculated from the end of curve 381 to the end of curve 382. Both times can be measured and an average taken of them if desired. Venous sensor calibration curve 383 occurs shortly after the introduction of the indicator, so it has a much sharper peak than curves 381 and 382. The time reference established by curve 383 is used preferably used for two purposes: (1) to establish a time window when the indicator bolus is expected back after traveling through the cardiopulmonary system, and (2) if the patient has recirculation in the hemodialysis shunt, then the indicator released through the venous outflow line is quickly recorded by the arterial sensor since it does not travel through the cardiopulmonary system, and the short time between the venous sensor signal of curve 383 and the arterial sensor signal of curve 381 helps to identify the presence of access recirculation.

Accordingly, it is to be understood that the embodiments of the invention herein described are merely illustrative of the application of the principles of the invention. Reference herein to details of the illustrated embodiments are not intended to limit the scope of the claims, which themselves recite those features regarded as essential to the invention.

What is claimed is:

1. A method for determining a shunt flow in a shunt connected between a first point and a second point in a circulating system, comprising the steps of:

(a) establishing a first flow rate in the circulating system;

(b) determining, during the first flow rate, a first flow time between spaced apart locations in the shunt;

(c) establishing a second flow rate in the circulating system;

(d) determining, during the second flow rate, a second flow time between the spaced apart locations in the shunt; and (e) determining a shunt flow from the first flow time, the second flow time, the first flow rate and the second flow rate.

2. The method of claim 1, further comprising determining the shunt flow according to the relationship:

$$Q_{sh} = \left( \frac{Q_{b1} - Q_{b2}\left(\frac{T_2}{T_1}\right)}{1 - \frac{T_2}{T_1}} \right),$$

where $Q_{sh}$ is the shunt flow, $Q_{b1}$ is the first flow rate, $Q_{b2}$ is the second flow rate, $T_1$ is the first flow time and $T_2$ is the second flow time.

3. The method of claim 1, wherein determining the first flow time and the second flow time includes measuring the passage of a dilution indicator at the spaced apart locations in the shunt.

4. The method of claim 1, further comprising establishing one of the first flow rate and the second flow rate as substantially zero.

5. The method of claim 1, further comprising employing a first average flow time between the spaced apart locations as the first flow time and employing a second average flow time between the spaced apart locations as the second flow time.

6. A method for determining a shunt flow in a shunt connected between a first point and a second point in a circulating system, comprising the steps of:

(a) establishing a first flow rate in the circulating system;
   (b) determining, during the first flow rate, a first line velocity in the shunt;
   (c) establishing a second flow rate in the circulating system;
   (d) determining, during the second flow rate, a second line velocity in the shunt; and
   (e) calculating a shunt flow from the first line velocity, the second line velocity, the first flow rate and the second flow rate.

7. The method of claim 6, further comprising calculating the shunt flow according to the relationship:

$$Q_{sh} = \left( \frac{Q_{b1} - Q_{b2}\left(\frac{V_1}{V_2}\right)}{1 - \frac{V_1}{V_2}} \right),$$

where $Q_{sh}$ is the shunt flow, $Q_{b1}$ is the first flow rate, $Q_{b2}$ is the second flow rate, $V_1$ is the first line velocity and $V_2$ is the second line velocity.

8. The method of claim 6, wherein determining the first line velocity includes measuring a time for passage of a dilution indicator between spaced apart locations in the shunt.

9. The method of claim 6, wherein determining the second line velocity includes measuring a time for passage of a dilution indicator between spaced apart locations in the shunt.

10. The method of claim 6, further comprising establishing one of the first flow rate and the second flow rate as substantially zero.

11. The method of claim 6, further comprising employing a first average line velocity between the spaced apart locations in the shunt as the first line velocity and employing a second average line velocity as the second line velocity as the second line velocity.

12. A method for determining a shunt flow in a shunt connected between a first point and a second point in a circulating system, comprising the steps of:

(a) establishing a first flow rate in the circulating system;
   (b) determining, during the first flow rate, a first value from which one a first flow time or a first line velocity corresponding to a first flow in the shunt can be determined;
   (c) establishing a second flow rate in the circulating system;
   (d) determining, during the second flow rate, a second value from which one a second flow time or a second line velocity corresponding to a second flow in the shunt can be determined; and
   (e) determining a shunt flow in the shunt corresponding to the first value, the second value, the first flow rate and the second flow rate.

* * * * *